(12) United States Patent
Engstad et al.

(10) Patent No.: US 9,956,245 B2
(45) Date of Patent: May 1, 2018

(54) GLUCAN COMPOSITIONS

(75) Inventors: Rolf Engstad, Tromsø (NO); Dag-Eirik Ramsøy, Tromsø (NO); Erik Steene, Tromsø (NO)

(73) Assignee: BIOTECH PHARMACON ASA, Tromsø (NO)

( * ) Notice: Subject to any disclaimer, the term of this patent is extended or adjusted under 35 U.S.C. 154(b) by 1272 days.

(21) Appl. No.: 13/989,588

(22) PCT Filed: Nov. 29, 2011

(86) PCT No.: PCT/GB2011/052359
§ 371 (c)(1),
(2), (4) Date: Aug. 9, 2013

(87) PCT Pub. No.: WO2012/073020
PCT Pub. Date: Jun. 7, 2012

(65) Prior Publication Data
US 2013/0309286 A1   Nov. 21, 2013

(30) Foreign Application Priority Data

Nov. 29, 2010 (GB) .................................. 1020193.7

(51) Int. Cl.
| | |
|---|---|
| *A61K 9/00* | (2006.01) |
| *A61K 31/716* | (2006.01) |
| *C08L 5/00* | (2006.01) |
| *C08J 3/075* | (2006.01) |
| *A61K 9/06* | (2006.01) |

(52) U.S. Cl.
CPC .......... *A61K 31/716* (2013.01); *A61K 9/0014* (2013.01); *A61K 9/06* (2013.01); *C08J 3/075* (2013.01); *C08L 5/00* (2013.01); *C08J 2305/00* (2013.01)

(58) Field of Classification Search
CPC .................................................... A61K 31/716
See application file for complete search history.

(56) References Cited

U.S. PATENT DOCUMENTS

| 5,082,936 A | 1/1992 | Jamas et al. |
| 5,322,841 A | 6/1994 | Jamas et al. |
| 5,579,769 A | 12/1996 | Yoshida et al. |

(Continued)

FOREIGN PATENT DOCUMENTS

| WO | 9530022 A1 | 11/1995 |
| WO | 9628476 A1 | 9/1996 |

(Continued)

OTHER PUBLICATIONS

Sletmoen, Marit, et al., "Review Higher Order Structure of (1,3)-β-D-Glucans and Its Influence on Their Biological Activities and Complexation Abilities," Biopolymers, vol. 89, No. 4, pp. 310-321 (2008).

(Continued)

*Primary Examiner* — Paul W Dickinson
(74) *Attorney, Agent, or Firm* — Rothwell, Figg, Ernst & Manbeck, P.C.

(57) ABSTRACT

The present invention relates to a gel composition comprising a glucan and a gelling agent, said composition having a melting point (gel to sol) above 37° C., as well as to the uses of this composition in therapy, in particular in wound healing.

43 Claims, 8 Drawing Sheets

(56) References Cited

U.S. PATENT DOCUMENTS

| | | |
|---|---|---|
| 6,242,594 B1 | 6/2001 | Kelly |
| 6,875,754 B1 | 4/2005 | Griesbach et al. |
| 2003/0185863 A1 | 10/2003 | Bengs et al. |
| 2006/0079481 A1 | 4/2006 | Engstad |
| 2006/0177492 A1* | 8/2006 | Yunoki .............. A61K 9/06 424/445 |
| 2009/0104141 A1 | 4/2009 | Ikeda et al. |
| 2009/0202640 A1 | 8/2009 | Paoletti et al. |
| 2010/0322923 A1 | 12/2010 | Seljelid et al. |
| 2011/0319442 A1* | 12/2011 | Leoni .............. A61K 9/0034 514/293 |

FOREIGN PATENT DOCUMENTS

| | | |
|---|---|---|
| WO | 99/21531 A1 | 5/1999 |
| WO | 02058711 A1 | 8/2002 |
| WO | 2004/039378 A1 | 5/2004 |
| WO | 2006/123173 A1 | 11/2006 |
| WO | 2007/062995 A2 | 6/2007 |
| WO | 2009/043319 A1 | 4/2009 |
| WO | 2009063221 A2 | 5/2009 |
| WO | 2009150651 A1 | 12/2009 |
| WO | 2011/011617 A1 | 1/2011 |

OTHER PUBLICATIONS

Steiner, E., et al., "Rheological properties of solutions of a colloid-disperse homoglucan from Schizophyllum commune," Progress in Colloid & Polymer Science, vol. 77, pp. 217-220 (1988).

Xu, Jingyuan, et al., "Micro-heterogeneity and micro-rheological properties of high-viscosity oat β-glucan solutions," Food Chemistry, vol. 103, pp. 1192-1198 (2007).

Pu Qinglin, "Research on Interaction of Yeast Glucan With Other Macromolecular Substances", China Excellent Doctoral and Master's Theses (Master) Engineering Science and Technology vol. I, Issue 2, Feb. 15, 2007, with English-language translation (94 pages with translation).

Matsuda, Kazuo (Jul. 1, 1999) "Separation and Purification Method of Polysaccharides" Seibutukagaku Jikkenhou, vol. 20, pp. 23-28, Center for Academic Publications Japan, Co. Ltd., Jul. 1, 1999, with English-language translation.

\* cited by examiner

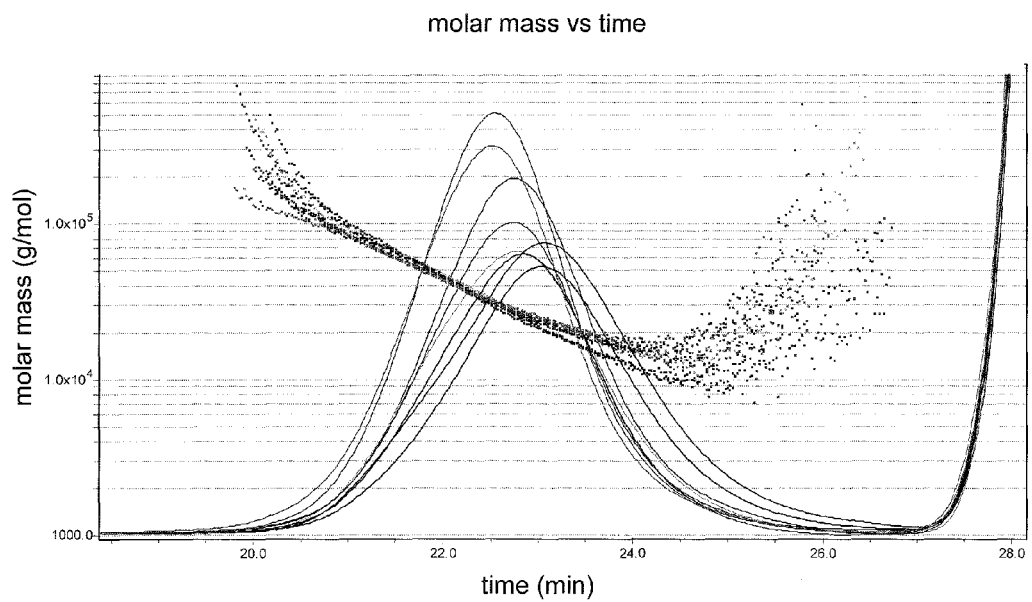
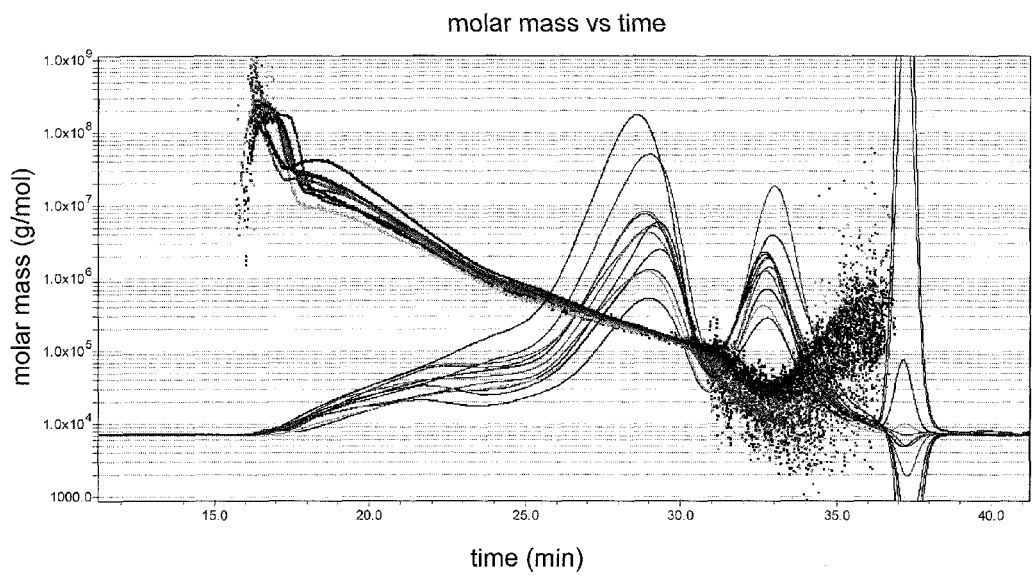
Figure 2:

GLUCAN COMPOSITIONS

This application is a filing under 35 USC 371 of International Application No. PCT/GB2011/052359, filed 29 Nov. 2011, which claims priority to GB Application No. 1020193.7, filed 29 Nov. 2010. These prior applications are incorporated herein by reference.

The present invention relates to new compositions comprised of gelling agents and glucans and to uses thereof as a pharmaceutical, as a medical device, incorporated in a medical device, as a nutraceutical, cosmetic product or the like. Preferably such compositions are used as primary wound dressings that may be directly applied to wound surfaces or provided on substrates to form a composite material. Methods for applying the glucan compositions to treat wounds are also described. Further described here are wound dressings and kits.

Glucans are a heterogeneous group of glucose polymers found in amongst others the cell walls of plants, bacteria, fungi and protozoa. Glucans have a backbone chain and in some cases side chains which, depending of the origin of the glucan, comprise β(1,3), β(1,4) and/or β(1,6)-linked glucosyl units. Depending upon the source and method of isolation, beta-glucans have various degrees of branching and type of linkage in the backbone and side chains. The frequency and type of linkage in the side chains is highly relevant to the molecule's biological activity. Glucans also differ highly in their molecular weight as well as in their tendency for chain aggregation which both are essential features for the efficacy profile of these molecules. Many glucans of fungal and yeast origin are in their native state insoluble in water, but can be made soluble either by acid hydrolysis or by derivatization introducing foreign groups like -phosphate, -sulphate, -amine, -carboxymethyl and so forth to the molecule.

In Europe, Asia and USA, beta-glucans especially from Bakers' yeast have long been employed as feed additives for animals, in cosmetics, as dietary supplement for humans, as immunomodulators e.g. in treatment of wounds, and as an active ingredient in skin cream formulations. Glucans have been employed in the treatment of cancer as shown in WO02/058711. Beta-glucans are, in this context, regarded as immunostimulants increasing the activity of white blood cells partly by inducing well regulated and local inflammatory reactions. Their use in the treatment of inflammatory bowel disease has also been described in WO 2009/063221. Further applications of glucans within wound treatment are described in EP 815144 and in U.S. Pat. No. 6,875,754 as well as for the treatment of asthma and allergy as described in U.S. Ser. No. 12/528,215.

Cereal glucans comprise generally unbranched chains of β(1,3) and a significant share of β(1,4) linkages while yeast glucans are made up of predominantly β(1,3) linked glucosyl residues with β(1,6) linkages acting as branch points for side chains which may comprise both β(1,3) and β(1,6) linked glucosyl residues. Other molecules classed as glucans include curdlan, a basically linear molecule made up of β(1,3) linked glucosyl residues without branches. Lentinan is a glucan with a β(1,3) linked backbone but incorporating single β(1,6) linked glucosyl residues attached essentially regularly to the backbone giving a haircomb structure of this molecule. The single β(1,6) linked glucosyl residues attached to the backbone equivalent to a β(1,3,6) linkage point but no further molecules are attached to this linkage point and thus glucans like lentinan do not have side chains. Other examples of this group of glucans are scleroglucan, laminarin and schizophyllan.

Variations in branching and the length and structure of the side chains lead to contrasting secondary and tertiary structures and thus biological activities. The higher order structures of glucans vary considerably and molecular weight, solubility and particle size will all influence activity in a generally unpredictable manner. Some products are extremely potent inducers of inflammatory cytokines in target cells, whereas others have the opposite effect, completely inhibiting cytokine release. Typical for many insoluble beta-glucan products is the induction of a whole range of inflammatory responses, where e.g. injection of insoluble beta-glucan formulations has been associated with granuloma formation, arthritis induction and increased susceptibility against gram negative sepsis. On the other side, soluble beta-glucans are not reported to be encumbered with such negative side effects, but their efficacy as immunostimulants have been known to vary substantially.

It has been shown (WO 95/30022), for example, that a glucan product derived from yeast which has been modified by glucanase treatment to selectively remove (1,6) linked side chains is more potent in stimulating the immune system of fish than a product with intact (1,6) linked side chains.

Glucans have great potential as therapeutic agents and adjuvants but the vast range of structural variability, problems of analysis with such large and complex molecules and the lack of understanding about mechanism of action and receptors for these molecules, means that there is still a great need for an improved glucan product, particularly one effective for wound treatment.

Beta-glucans are known to be so-called Pathogen Associated Molecular Patterns as they are found at the surface of a number of pathogenic (micro)organisms, especially fungi. Higher organisms have thus evolved mechanisms for recognizing these types of structures in order to find and destroy intruders belonging to this class of organism. In mammals the so called innate immune cells express specific receptors recognizing beta-glucans, and one of the most prominent receptors is called Dectin-1, but other receptors are also involved in the recognition or signal transduction induced by beta-glucans amongst these are CD11b/CD18 (CR3), and toll receptors 2 and 4 (TLR2 and TLR4). Of the cells involved in recognizing beta-glucans are the typical phagocytes of the innate immune system, i.e. monocyte, macrophages, dendritic cells, and granulocytes, but also Natural Killer cells as well as a number of endothelial cells and other more tissue specific cells have the ability to express beta-glucan receptors.

The crucial step in inducing a biological response in the target cells is the initial binding to the receptor and furthermore, it seems, the ability of the beta-glucan formulation to cross-link a sufficient number of receptors in order to induce an adequate signal-transduction into the cell. The present invention describes a product that has the ability to induce a specific type of biological activity. This is in contrast to insoluble products that could induce a massive response by cross-binding a large number of receptors and secondly be phagocytosed, which due to the nature of the insoluble (or "crystalline like") glucan leads to lysosomal rupture within the cell inducing NLRP inflammasome activation. Insoluble beta-glucans may also induce ROS (reactive oxygen species) that also would trigger inflammasome activation leading to an unfavorable inflammatory reaction. The current invention describes beta-glucan products that are able to induce a significant inflammatory response that would activate several immune mechanisms, but without triggering inflammasome activation that is typical for a number of (aggregated insoluble) beta-glucan products.

Glucan products are usually particulate or in some cases completely soluble in aqueous solutions, the latter either giving a fluid clear solution as described, for example, in U.S. Pat. No. 5,322,841 or some giving a viscous solution as described in Steiner et al (Prog Colloid Polymer Science 77, 1988). True gel forms of soluble beta-glucans are unusual and especially of soluble yeast glucans, but the present gel product has been found to provide excellent biological activity, in particular in wound healing, as compared to other glucan products. In addition to an outstanding pharmaceutical or medical device efficacy profile, in wound healing it is of utmost importance to apply a pharmaceutical or medical device in a manner which secures the moisturization of the wound. In addition the final products must cover and preferably stick to the wound to avoid infections and provide for an administration profile as deemed relevant by a physician or necessary due to the type of wound. Usually, glucans in their particulate, semi-soluble or liquid form do not solve these basic requirements either because they are not effective; they are in a state which is not applicable for wound healing purposes, or both. The glucan composition of the present invention combines these necessary characteristics thus making it useful for all applications where a glucan gel composition may find a proper use. In addition to strictly topical applications, other uses include oral and/or mucosal administration, such as in treating diseases of the gastrointestinal tract or in the oral cavity. The excellent adhesion properties of the glucan composition according to the present invention enables coverage of the mucosal lining at the site of action and thus accelerates the healing process. Thus the glucan compositions of the invention may also have particular utility in the treatment of oral mucositis.

Surprisingly, the inventors of the present invention noticed that a combination of a beta glucan and a gelling agent leads to a synergistic effect and thus improved wound healing. Without being bound to a specific theory, a possible explanation for this synergy effect could be due to the optimized presentation of beta glucan to Pattern recognition receptors (PRRs) on immune cells. These PRRs are proteins expressed in the cell membrane of cells in the innate immune systems. These PRRs are designed to recognize pathogen-associated molecular patterns (PAMPs) associated with microbial pathogens and cellular stress. PAMPs instruct phagocytes and antigen-presenting cells to further mature and activate an additional battery of effector functions. Thus, a granulocyte or macrophage that has not been stimulated with PAMPs will be insufficiently able to kill and destroy target cells and microbes. PAMPs are also fundamental in immunity by ensuring that responses are mounted to relevant stimuli (e.g. microbes) and not to self-antigens. Three central PRRs known to contribute in the recognition of PAMPs are Complement receptor 3 (CD11b/CD18), the heterodimer of Toll-like receptor 2 and 6, and the Dectin-1 receptor. The effective stimulation of these receptors is a crucial step in activation of the innate immune system and results in an altered state of all the cells involved. Based on the positive results of a combination between such a beta glucan and a gelling agent, it seems that the gelling agent may act as means for the correct association and cross-binding of beta glucans to the PRRs located on these receptors thereby improving the efficacy of the wound healing cascade.

Thus, in one aspect, the present invention provides a gel composition comprising a glucan and a gelling agent, which composition has a melting point (gel to sol) above 37° C. The gelling agent preferably comprises or consists or consists essentially of one or more carbohydrates/polysaccharides (other than a glucan) and is present at a concentration which serves to stabilize the gel structure. The glucan is present in the formulation as a gel and thus is a soluble rather than particulate glucan form. Preferably the glucan on its own forms a gel when dissolved in water at a concentration ≥1% (e.g. 1.5-6%) at 25° C. and neutral pH.

When combined with a gelling agent the concentration of the beta-glucan component can be reduced to ≥0.1% and the desired gel properties could be obtained by the added gelling agent. The upper limit of beta-glucan content would be determined by the concentration and nature of the added gelling agent, but would typically be less than 4%. The final product wherein beta-glucan and a gelling agent is combined, would be formulated to have the desired wound healing abilities as described above. Examples include 1 or 2% soluble yeast beta-glucan combined with 1 or 1.5% high molecular weight carboxymethylcellulose giving a stable gel and having improved wound healing capabilities as compared to the two when used as single agents. When mixed the gelling agent would allow for arranging the molecular organisation of the beta-glucan in a favourable supramolecular type of organisation. For a pharmaceutical application of the novel gel, the organisation of beta-glucans within the gel is stabilised in a form that enables cross-binding of receptors on the surface of the target cell population, thus giving a desired immunopotentiating activity, but without having the negative effects of an aggregated insoluble beta-glucan formulation. Preferably the glucan is a yeast glucan and has a weight average molar mass on a single chain basis of 15,000 to 50,000 g/mol and a weight average molar mass in aqueous solution on an aggregate basis of 4 to $20\times10^5$ g/mol.

A "single chain" refers to an individual glucan molecule, i.e. one in which the glycosyl residues are covalently linked. "Aggregates" form through hydrogen bond interactions and define a supramolecular or higher order structure. Such associations are less permanent than provided by covalent bonding but the methods described herein result in recognisable patterns of aggregation, whose average molar mass can be analysed using the techniques referred to herein. The "aqueous solution" is typically pH 7.

It is appreciated that an aqueous solution can be in gel form. The gels of the invention are preferably aqueous solutions, i.e. hydrogels. The gel compositions are preferably hydrated hydrocolloids. Hydrated hydrocolloids may display both elastic and viscous behaviour. Hydrocolloids typically gel when intra- or inter-molecular hydrogen bonding is favoured over hydrogen bonding to water, to a sufficient extent to overcome the entropic cost.

The gelling agent is preferably a polymer which is itself able to form a hydrogel in aqueous solution and, in combination with the glucan, can enhance the gel-forming properties of the glucan component.

Examples of preferred gelling agents are those originating from cellulose, bacteria or algae like hydrogels, alginates, gellan gums as well as cellulose polymers and derivatives like carboxymethyl cellulose, methylcellulose, hydroxypropyl cellulose, hydroxyethyl cellulose, hydroxypropyl methylcellulose and hydroxypropyl methylcellulose phthalate. Some of those gels also have incorporated additional components like silver. Thus the gelling agents are preferably non-glucan polysaccharides. The gelling agents are preferably hydrocolloids and suitable hydrocolloids may be proteinaceous instead of sugar based. In all cases the gelling agents may be naturally occurring agents, derived therefrom by chemical or other processing methods, or entirely synthetic.

Gums such as tragacanth and xanthan gum; sodium alginate; gelatin and Gellan gum may be used as gelling agents. As a representative of this group, gellan gum a bacteria-derived product, also branded as AppliedGel, Phytagel or Gelrite is frequently used as a thickener, emulsifier, and stabilizer. Gellan gum is an anionic, high molecular weight, deacetylated exocellular polysaccharide gum produced as a fermentation product by a pure culture of *Pseudomonas elodea*, with a tetrasaccharide repeating unit of one α-L-rhamnose, one β-D-glucuronic acid and two β-D-glucose residues. The tetrasacharide repeat has the following structure: $[D\text{-}Glc(\beta1\rightarrow4)D\text{-}GlcA(\beta1\rightarrow4)D\text{-}Glc(\beta1\rightarrow4)L\text{-}Rha(\alpha1\rightarrow3)]_n$. The tetrasacharide units are connected with each other using an (α1→3) glycosidic bond. The exact molecular formula of gellan gum may vary slightly (e.g., depending on the degree to which the glucuronic acid is neutralized with various salts). Gellan gum has the characteristic property of temperature-dependent and cation-induced gelation. There are three basic forms of gellan gum product which have been characterized and are distinguished by their 1) polysaccharide content, 2) the percent of o-acetyl substitution on the polysaccharide and 3) the protein content (including nucleic residues and other organic nitrogen sources). It is available in two forms (high or low acyl content). The acyl groups have a profound influence on gel characteristics. The high acyl form produces soft very elastic and non-brittle gels, while the low acyl form produces firm, non-elastic and brittle gels. Gellan gum is practically non-toxic to rats when administered as a single large dose (5 g/kg b.w.) in diet or via gavage.

Products like carboxymethyl cellulose or methylcellulose are representatives of the group of gelling agents which is derived from cellulose which is a polymer of β-D-Glucose which is oriented with —$CH_2OH$ groups producing long, unbranched chains. Cellulose is the major structural material of plants. Cellulose may be modified to replace some or all the hydroxyl groups with other groups like methoxide (—$OCH_3$) groups and carboxymethyl (—$CH_2$—COOH) groups. Methyl cellulose is synthetically produced by heating cellulose with caustic solution (e.g. a solution of sodium hydroxide) and treating it with methyl chloride. Different kinds of methyl cellulose can be prepared depending on the number of hydroxyl groups substituted. Carboxymethylcellulose (CMC) is formed by the reaction of cellulose with alkali and chloroacetic acid. Different preparations of CMC may have different degrees of substitution, but it is generally in the range 0.6-0.95 derivatives per monomer unit. CMC molecules are somewhat shorter, on average, than native cellulose with uneven derivatization giving areas of high and low substitution. Most CMCs dissolve rapidly in cold water and are mainly used for controlling viscosity without gelling as CMC, at typical concentrations, does not gel even in the presence of calcium ions). Its control of viscosity allows use as thickener, phase and emulsion stabilizer, and suspending agent. CMC can be also used for its water-holding capacity as this is high even at low viscosity; particularly when used as the $Ca^{2+}$ salt. Carboxymethyl cellulose (CMC) or cellulose gum is often used as its sodium salt, sodium carboxymethyl cellulose.

Alginate is the most abundant marine biopolymer and, after cellulose, the most abundant biopolymer in the world. The major source of alginate is found in the cell walls and the intracellular spaces of brown seaweed, such as giant kelp (*Macrocystis pyrifera*). Alginates are also synthesized by some bacteria (e.g. *Azotobacter* and *Pseudomonas* species). Alginates are the salts and esters of alginic acid. The chemical constituents of alginate are random sequences of chains of β-D-mannuronic and α-L-guluronic acids attached with 1→4 linkages. Alginates are insoluble in water, but absorb water readily. The use of alginate as an immobilizing agent in most applications rests in its ability to form heat-stable strong gels which can develop and set at room temperatures. It is the alginate gel formation with calcium ions which has been of interest in most applications.

Other gel-forming agents to be used in accordance with the present invention are, but are not limited to, carbomers; hydrophilic polymers such as polyethylene oxides, polyoxyethylene-polyoxypropylene copolymers, and polyvinylalcohol.

The combination of the present invention can be used to prepare effective glucan containing compositions in gel form with any soluble glucan starting material. The synergistic effect observed means that for a given concentration of glucan, the gel composition will demonstrate superior activity. Soluble glucan products are known to the skilled man and some are commercially available. The glucans are typically derived from yeast, preferably form *Saccharomyces cerevisiae*. The basic molecular structure of these glucans is typically a β-1,3-backbone (meaning a chain of glucose molecules linked by β-1,3 linkages), in addition to β-1,3 side chains (meaning a chain of at least two glucose molecules linked by β-1,3 linkages) and a β-1,3,6-linkage point linking the side chains to the backbone. In addition, glucans from yeast comprise β-1,6 linkages which may be linked to the side chains or directly to the backbone. Further types of linkages do exist but at a comparably low level. Other yeasts which may provide a source for the glucan include Brewers yeast, *Candida* sp. like *Candida albicans, Candida cloacae, Candida tropicalis, Candida utilis, Hansenula* sp. like *Hansenula wingei, Hansenula arni, Hansenula henricii* and *Hansenula americana, Histoplasma* sp., *Kloeckera* sp., *Kluyveromyces* sp. like *Kluyveromyces lactis, Kluyveromyces fragilis, Kluyveromyces polysporus, Pichia* sp., *Rhodotorula* sp., *Saccharomyces* sp. like *Saccharomyces delbruekii, Saccharomyces rosei, Saccharomyces microellipsodes, Saccharomyces carlsbergensis* or different *Saccharomyces* strains like *Saccharomyces cerevisiae* R4 (NRRL Y-15903) and R4 Ad (ATCC No. 74181), *Schizophyllum* sp., *Schizosaccharomyces* sp. like *Schizosaccharomyces pombe, Torula* sp. and *Torulopsis* sp.

However, the glucans may be derived from other suitable sources, e.g. bacterial, fungal or cereal glucans. Lack of gel forming ability of the beta-glucan per se can be compensated for by the gel forming ability of the agents like CMC, as described above, giving a product with the desired wound healing properties. The therapeutic activities of various glucans are well documented in the art and the composition of the present invention may be used to enhance activity of glucans in general, in particular in wound healing where the physical form and inter-molecular structure of the glucan product has been shown, by the present inventors, to be particularly significant. Without wishing to be bound by theory, a rule of thumb is that the higher the weight average molar mass on a single chain basis of the glucan used in the compositions of the invention, the more efficacious gels may be produced.

The side chains of a gel forming glucan of the present invention usually comprise 2 or more β(1,3) linked glucosyl units. According to the present invention, single molecules linked to a main chain are not regarded as "side chains".

The gel-forming glucans preferably have side chains of, i.e. consisting or consisting essentially of, β(1,3) linked glucosyl units (e.g side chains of at least 2, 5, 10 or 20 linked glucosyl residues). In addition to the β(1,3) linked side chains, the glucans may also have one or more β(1,6) linked side chains. By altering the chains of the structure it is possible to alter the characteristics of the final product. There are many different ways of altering glucans including enzyme-treatment, use of acids like formic acid or hydrochloric acid or different bases as well as by other means. Preferred glucans are those which have been treated by acid (e.g. formic acid) or enzyme or any other suitable method to significantly reduce or eliminate the number of repetitive (1,6)-linked glucose molecules within the glucan. These (1,6)-linked glucosyl moieties would normally be found in the side chains of beta-glucans derived from yeast. The resulting glucans have β(1,3) main chains and β(1,3) side chains which are linked thereto through a single β(1,6) linkage which is not cleaved off by the elimination treatment.

The preferred glucans are essentially free of repetitive β(1,6) linked glucosyl residues. The single (1,6) linkages at the branch points (the β(1,3,6)-branching points) do not provide 'repetitive' β(1,6) linked glucosyl units. By 'essentially free' is meant less than 6%, preferably less than 4% and most preferably less than 3% of the total glucosyl units.

Some treatments, such as enzyme treatments, may leave up to 4 beta-1,6-linked, but typically 2 beta 1,6 linked glucosyl units uncleaved in the side chains. Such molecules are also 'essentially free' of repetitive beta 1,6-linked glucosyl units.

The distribution of linkages within preferred glucans may be represented as follows:

| Type of linked glucosyl residue | % |
|---|---|
| β(1,3) | 80-98 |
| β(1,6) | 0-6 |
| β(1,3,6) | 1-8 |
| Terminal | 0.01-6 |

β(1,3,6) refers to branch point residues which are (1,3) linked in the backbone and participate in a (1,6) connection to provide a side chain.

The glucan could be in the form of a single, extracted fraction or two or more different fractions with different average molecular weights.

The glucans are preferably underivatized in terms of chemical modifying groups.

The molar mass of glucans can be determined in different ways. In the case of a soluble glucan product the molar mass is conveniently measured by SEC-MALS-RI (size exclusion chromatography with multi-angle light scattering and refractive index detection) analysis, and such analysis provides a weight average molar mass value ($M_W$) for the sample as well as the distribution of different molecular weights within the sample. In the present invention, the weight average molecular mass ($M_W$) is defined as follows:

$$M_w = \frac{\Sigma n_i M_i^2}{\Sigma n_i M_i} = \frac{\Sigma c_i M_i}{\Sigma c_i}$$

Where $n_i$ is the number of molecules with molar mass $M_i$. The weight concentration $c_i$ of molecules with molar mass $M_i$ is proportional to the molar mass $M_i$ and the number of molecules $n_i$.

$$c_i = M_i n_i => n_i = c_i / M_i$$

The weight concentration for each slice of the chromatogram is measured by the RI-detector while the molar mass for each slice in the chromatogram is measured by the MALS-detector in combination with the RI-detector. The calculations are based on light scattering theory.

Specifically, the average molecular mass (for single chains) is determined by SEC-MALS-RI in DMAc with 0.5% LiCl (dimethylacetamide with 0.5% lithium chloride) assuming a do/dc of 0, 12 for the glucan in this solvent. The DMAc/LiCl solvent fully dissolves the said glucan into single chains and subsequent SEC-MALS-RI analysis with DMAc with 0.5% LiCl as eluent therefore gives a measure of the molecular weight distribution on a single chain level. In short, the analysis of the glucan in DMAc/LiCl involves dissolution of the dry glucan in the solvent at a concentration of approximately 3 mg/ml by stirring the solution at room temperature overnight and heating it at 100° C. for 1 h, prior to the analysis by SEC-MALS-RI using 3× PlgelPLgel Mixed-A LS columns and DMAc/with 0.5% LiCl as eluent. The weight average molar mass for the glucan on a single chain basis is preferably 15,000 to 50,000 g/mol, more preferably 25,000 to 45,000 g/mol, most preferably 30,000 to 40,000 g/mol.

In aqueous solution the weight average molar mass of the mainly higher order glucan structures and aggregates present is preferably $4-20 \times 10^5$ g/mol, more preferably $5-15 \times 10^5$ g/mol, and most preferably $6-12 \times 10^5$ g/mol. These averages are preferably calculated when very large aggregates, i.e. molar mass above $1.0 \times 10^7$ g/mol, are excluded. The analysis of the glucan in aqueous solution involves diluting the gel solution to approximately 3 mg/ml in 0.1M $NaNO_3$/0.02% $NaN_3$, heating to 100° C. in a capped glass tube for 30 min, cooling to room temperature, filtrating through a 0.2 μm syringe filter, and analysis by SEC-MALS-RI using TSKgel G5000 PWXL+TSKgel G4000 PWXL columns and 0.1M $NaNO_3$/0.02% $NaN_3$ as eluent. Similar set-ups with for example 0.05 M $Na_2SO_4$/0.01 M EDTA as solvent/eluent gives equivalent results. The combination of molar mass values for the single chains and the higher order structures/aggregates in aqueous solution gives a good indication of the molecular and supramolecular structure of the preferred glucans used in the formulations of the invention.

The above glucan gels are examples of glucans in accordance with the present invention. These glucan products are characterized by being in gel form at 25° C. and at a pH between 4 and 8. These glucan gels are further characterised by their viscosity profile exemplified by the melting temperature of the gels (gel to sol) of above 30° C. and up to approximately 80° C., preferably above normal body temperature.

The gel melting point for a glucan product, i.e. the gel→sol transition temperature, is conveniently determined by small strain oscillatory measurements using a Stresstech HR rheometer or similar and examining the viscoelastic changes during cooling (70→10° C.) and heating (10→70° C.) of the glucan solution. Another way of determining approximate melting temperature of the gel is to measure the viscosity (e.g. using a rotational viscometer) of the gel at sequentially higher temperature until the viscosity is essentially gone and the gel has transformed into a solution.

The preferred glucans of the present invention trigger the expression of TNFα and CXCL2/MIP2α in mouse peritoneal macrophages. A weak induction of TNFα is also seen in human myeloid dendritic cells derived from peripheral blood monocytes.

The effect of the preferred beta glucans on release of TNFα is dose-dependent and appears to diminish at glucan concentrations above a certain threshold value eg. 2-4 µg/ml in a variant of the RAW cell line overexpressing the beta glucan receptor dectin-1. A moderate to low induction of TNFα and CXCL-2 is special to the products of the present invention. Both TNFα and CXCL-2 are instrumental in wound healing. The murine chemokine CXCL2 stimulates cell migration and angiogenesis, and can be used as surrogate marker for angiogenic activity in the inflammatory granulation tissue.

The preferred glucans of the present invention do not trigger a powerful expression of IP-10 (CXCL-10). IP-10 is a member of the alpha or cysteine-X amino acid-cysteine (CXC) chemokine family of chemotactic cytokines. High levels of IP-10 expression have been detected in a number of chronic human inflammatory conditions, including psoriasis, a common inflammatory disease of the skin. Patients have generally shown an abnormal wound healing response characterized by a more intense inflammatory phase and a prolonged and disorganized granulation phase with impaired blood vessel formation. The glucans of the present invention should not enhance the LPS-induced expression of IP10 from human dendritic cells, and preferably inhibit the LPS induced expression of IP-10 from macrophages harvested from db/db mice. This shows that the preferred glucans according to this invention turn on beneficial elements of the wound healing process while they turn off inhibitors leading to a prolonged healing phase.

In addition, the gel glucans of the invention preferably activate the complement system.

The glucan compositions of the present invention have excellent in vivo efficacy as wound healing agents, as shown in the Examples.

The glucan used in the composition of the present invention may be a more potent variant, specifically soluble beta glucans with an ability to induce the differentiation of human myeloid dendritic cells towards an inflammatory phenotype, significantly stimulate TNF-alpha secretion and also induce production of G-CSF and IL-10 by dendritic cells. In all cases, the secretion of CXCL-10 should be basically at baseline level, and unaffected by the treatment described herein ie. combination with a gelling agent. This is important and illustrates that the preferred glucan stimulates the secretion of a specific set or combination of cytokines. The preferred glucan can also stimulate macrophages from diabetic mice (db/db) to secrete PGE2 and GM-CSF.

The glucan gel used in the Examples in accordance with the present invention was an aqueous gel and while the gel form can be confirmed by visual inspection, the non-newtonian viscosity profile and the pseudoplastic and thixotropic nature of the glucan gel may also be determined by viscosity measurement e.g. by using a rotational viscometer. A 2% glucan gel as used in the Examples has a viscosity of at least 1000 cP, preferably at least 1500 cP, measured at 25° C. and a rotational speed of 10 rpm using a Brookfield DV-II+ Pro Programmable viscometer with a small sample adapter and spindle SC4-31 (corresponding to a shear rate of 3.40 sec$^{-1}$). A convenient method for measuring the viscosity of this pseudoplastic and thixotropic gel is to use a so called up-down rate ramp, for example starting at 2 rpm and going up in 2 rpm increments to 10 rpm and then going back down again in 2 rpm steps. The data from such an experiment can both demonstrate the pseudoplastic (decreasing viscosity with increasing shear rate) and thixotropic (decreasing viscosity over time while subjected to shear) characteristics of the gel as well as provide a measure of e.g. 10 rpm viscosity.

Glucans with the above advantageous properties for use in the compositions of the invention can be prepared by either of the two methods described below and in more detail in the Examples. In each case a solution of glucan molecules is taken and then treated either by heating (or other energy source) or with a chemical agent which destroys the existing inter-molecular hydrogen bonds. Then that product is cooled rapidly to form a gel or an agent is added which serves to encourage the reformation of the hydrogen bonds between the glucan chains. As discussed below, the gelling agent may be added prior to the treatment step to dissociate inter (and potentially intra)-chain hydrogen bonds. Alternatively the gelling agent may be added after that step but prior to the treatment step which results in formation of hydrogen bonds and thus gel formation. Thus, in a further aspect, the present invention provides a method of producing a gel composition as defined herein which comprises:

a) treating an aqueous solution of glucan molecules, optionally together with a gelling agent, to dissociate the glucan's hydrogen bonds;

b) optionally adding gelling agent to the product of step a); and then c) treating the aqueous solution to reform hydrogen bonds within the glucan. In particular, hydrogen bonds are formed between glucan chains/molecules, these bonds are "reformed" because after step a) the amount of hydrogen bonding was significantly reduced and is increased in step c). They are not "reformed" in the sense that the hydrogen bonding pattern within the starting material is regenerated, instead a different pattern is generated by the process.

According to a preferred method of producing a composition as defined above, an aqueous solution of glucan molecules is heated to a temperature of 120-130° C., preferably 120-125° C., and held at that temperature for 10-30 minutes, the glucan solution is then cooled to a temperature of 35-50° C., preferably 35-40° C., over a time period not greater than 80 minutes, preferably less than 60 minutes, e.g. 50-60 minutes. Shorter cooling times (e.g. 25-50 minutes) may be appropriate for smaller volumes (e.g. less than 100 liters), the above figures relate to a starting product volume of 220 liters. The above cooling times are considered rapid, as they do not rely on an unassisted return to room temperature. By doing this a highly randomly organized "haystack" gel will be created without having the typical triple helical structure of "annealed" beta-glucan chains. According to this heating and cooling step, a solubilised beta-glucan preparation is energized in order to essentially solubilise the glucan gel, thus breaking up existing higher order structure and inducing a random organization with a large proportion free single chain molecules By rapid cooling the molecules are "frozen" to a new molecular conformation by rapidly establishing intermolecular interactions wherein the product does not primarily form triple helical structures. The molecules are thus frozen in a more random molecular position.

The heating is preferably performed in an isolated and agitated tank large enough to hold the entire batch of product, with a jacket or similar structure to enable the heating of the outside of the tank. The batch size, the capacity of the heating system, the volume to surface ratio of the tank and the effect of the agitator should be balanced in such a way that the whole batch may be heated to the specified temperatures within a reasonable time period, while ensuring a homogeneous heating of the whole batch. Alternatively the energizing step may take place after the product has been filled in its final container, either by heating in an autoclave or by alternative forms of energizing, e.g. ultrasound or micro waves.

If the energizing step has been performed for the whole batch in a tank, the active cooling is preferably performed in the same tank, and will require the ability to use the jacket of the tank to cool the tank surface. Again the batch size, the capacity of the cooling system, the volume to surface ratio of the tank and the effect of the agitator should be balanced to allow cooling to take place within the specified time, while ensuring a homogeneous cooling of the whole batch. This initial cooling should be followed by the filling of product into final containers, and subsequent cooling of the containers to room temperature. Preferably the cooling step is performed immediately after the heating step, i.e. immediately (in so far as is practical with the equipment concerned) after the glucan has been held at the elevated temperature for 10-30 minutes.

A suitable procedure for performing the heating and cooling steps in an industrial process is described in Example 1.

If the energizing step has been performed in the final containers, these containers should be cooled to room temperature within the time frame described above.

The heating and cooling step described above may be repeated, e.g. once more.

The concentration of glucan in aqueous solution prior to the heating and rapid cooling step is preferably 1.5-6%.

The above heating and cooling step may be performed on any aqueous solution of glucan molecules; preferred glucans, including glucans with modified branching, are discussed above and the glucan solution will preferably be a yeast glucan solution. The starting material for the heating and cooling steps may itself be in gel form, thus heating results in a transition to sol and cooling results in the formation of a different gel structure to that of the starting material. The weight average molar mass ($M_w$) of the glucans in the starting solution is preferably high, preferably, on a single chain basis, the weight average molar mass of glucans in solution is above 15,000, more preferably above 20,000, most preferably above 25,000 g/mol. Suitable methods for determining these mass values are given above.

Glucans are generally extracted from their source material (e.g. fungi, yeast or cereal) in particulate form but methods of generating soluble forms from particulate glucans are known in the art and include acid or alkali treatments, such as the formolysis step described in WO 95/30022. Soluble glucan products from cereals like barley are available from Sigma Chemical. A particulate starting material, such as may be prepared by the protocol in Example 1 of WO 95/30022, will preferably be solubilised by heating in formic acid for at least two hours. Formolysis performed on particulate glucan starting material may conveniently cause selective removal of any β(1,6) linked glucosyl side chains as well as solubilising the particulate glucan.

The above production method may also comprise a preliminary heating step, prior to the above described heating and rapid cooling step, where the formic acid treated product is boiled (>100° C.) for at least 30 mins. After the product has cooled it is preferably treated to remove particulate materials by regular methods know in the art e.g. by centrifugation or filtration.

The particulate glucan which is treated to yield a soluble form for further processing in accordance with the invention is preferably derived from cell walls, in particular yeast cell walls, which have had the protein components and other remnants like mannan and chitin removed therefrom e.g by washing.

One example of a suitable particulate yeast glucan product is produced by Biotec Pharmacon ASA which is derived from Bakers Yeast (*Saccharomyces cerevisiae*) and known as NBG Cos®. Another example of particulate glucan raw materials are whole glucan particles like the product Imprime WGP™. NBG Cos® is a natural underivatized (in terms of chemical modifying groups) particulate β(1,3)/(1,6) glucan, characterised by NMR and chemical analysis to consist of polymers of beta-1,3-linked D-glucose containing side-chains of beta-1,3 and beta-1,6-linked D-glucose.

As an alternative to the above protocol, the same starting solution of glucan molecules may be treated with an agent able to dissociate hydrogen bonds between glucan chains, followed by treatment with an agent able to restore inter-chain hydrogen bond interactions.

One such agent to dissolve hydrogen bonds between OH-groups in the poly-glucose chain would be sodium hydroxide (NaOH) in a sufficient concentration that would deprotonise the numerous OH-groups in the chains. This would lead to a complete dissociation of all intermolecular bonds typical for these high molecular weight glucans resulting in a random organization of the chains in solution. By neutralizing the solution by addition of acid to neutralize the alkali, the OH-groups are reformed and new hydrogen bonds between the chains can be established.

Using NaOH as the agent would typically need the addition of e.g. 2M NaOH solution to a final concentration of above 50 mM, or more preferably about 150 mM to a soluble glucan concentration of 1-6% in aqueous solution, more preferably 1.5-4% or most preferably 2-4%. In order to neutralize the solution an equimolar amount of e.g. 2M hydrochloric acid (HCl) can the added to the solution under agitation for a brief period which is long enough to ensure an efficient neutralization, e.g. less than a minute for a volume like 1000 ml, whereafter the solution is left to establish the gel-conformation, e.g. 1-10 minutes for a volume of 1000 ml. Any other agent having the ability to dissociate the hydrogen bonds could replace NaOH, and any other agent able to rapidly allow re-establishment of the hydrogen bonds forming a "haystack" type of gel could replace HCl. The skilled man is aware of other agents which can disrupt and then restore hydrogen bonds, bases and acids, are particularly convenient as one can be readily balanced against the other to neutralize the impact of the agent which has disrupted hydrogen bonds. Other strong acids such as formic acid or sulphuric acid may be used. Also other alkali salts including, but not limited to, potassium hydroxide, lithium hydroxide, and calcium hydroxide, as well as possibly so called superbases such as sodium hydride or sodium amide, can be potential agents for deprotonation and disruption of hydrogen bonds. Any acid with the appropriate quality can be utilized to neutralize the solution in order to restore hydrogen bonds—this includes, but not limited to, phosphoric acid, acetic acid, and citric acid. Urea or formamide are also commonly used to disrupt hydrogen bonds and could possibly be used in this process. The nature of the restoring agent would be dictated by requirements set by the downstream applications, and specifically the presence of salts.

It will be appreciated that in a system involving large and complex organic molecules, it is not feasible or necessary to ensure that all hydrogen bonds have been disrupted or that all molecular chains participate in significant hydrogen bonding after conditions have been applied which enable the restoration of hydrogen bonding. However, the conditions applied will be such as to radically alter the organization and degree of hydrogen bonding in the glucan solution overall. The skilled reader is aware of the impact on a glucan solution of, for example, 150 mM NaOH and the concentration of other hydrogen bond breakers can be selected accordingly. The purpose of the second step, where conditions are provided which allow reestablishment of hydrogen bonds, is effectively to rapidly neutralise or reverse the effect on the potential for intermolecular electrostatic interactions caused by the addition of the hydrogen bond breaker. Thus the nature and concentration of this second agent will follow from the selection of the hydrogen bond breaker.

In an industrial process the steps will conveniently be performed in a tank large enough to hold the entire batch of product.

The steps of hydrogen bond disruption and then restoration as described above may be repeated, e.g. once more.

The composition preferably comprises 0.1-6% glucan in an aqueous solution, preferably the composition comprises 0.2-2% glucan in an aqueous solution. The use of different concentrations is certainly dependent on the purpose and the different modes of administration. A gelling agent or a viscosity agent or an appropriate blend of such agents will typically be present at 0.2-3%, preferably 0.25-2%, more preferably 0.75-1.75%, most preferably 1-1.5% by weight of the composition.

To aid gel formation and increased viscosity, other gel forming agents such as, but not limited to, acacia, agar, acrylic acid and its derivatives, polyacrylic and its derivatives such as polybutylmethacrylate and polymethacrylic acid, polymethacrylate, ascorbyl palmitate, carbomer, carnauba wax, gellan gel, alginic acid and the corresponding salts, cellulose derivatives such as cellulose acetate phthalates, rosca mellose sodium, hydroxyethyl cellulose, hydroxypropyl cellulose, hydroxypropyl methylcellulose, ethyl cellulose and related compounds, carboxymethylcellulose and its salts, hydroxypropyl methylcellulose phthalate, hypromellose phthalate, cetyl alcohol and derivatives, microcystalline wax, poloxamer, polyethylene glycol, polyurethane, polyvinyl acetate, polyvinyl acetate phthalate, polyvinyl alcohol, silicone rubber and derivatives, shellac, triglycerides derivatives, and combinations thereof are used.

The composition may consist a humectant or emollient agent such as, but not limited to, glycerine, propylene glycol, triacetin, cyclomethicone, polydextrose, and combinations of thereof.

As examples of combinational gels in accordance with the invention would be 1 or 2% soluble glucan mixed with a high molecular weight carboxymethyl cellulose to a final concentration of the latter at 1 or 1.5%. The formulation gel can be established by adding the appropriate amount of CMC in a 1 or 2% aqueous solution of glucan. After CMC is completely dissolved, the formulation is heated to above or about 100° C. and rapidly cooled to form a gel with the appropriate properties.

Another example of a gel formulation is a 2% glucan mixed with a gellan gel to a final concentration of 0.3%, where the glucan solution is heated to above or about 100° C. and the appropriate amount of gellan gum dried powder is added. The powder is left to dissolve and cool to about 50° C. where after $CaCl_2$ to a final concentration of about 5 mM is added to induce gel formation. The solution is then rapidly cooled to stabilise the gel formed.

A third example of a gel formulation is a 0.5% glucan mixed with a gellan gel to a final concentration of 0.5%, where the glucan solution is heated to above or about 100° C. and the appropriate amount of gellan gum dried powder is added. The powder is left to dissolve and cool to about 50° C. where after $CaCl_2$ to a final concentration of about 5 mM is added to induce gel formation. The solution is then rapidly cooled to stabilise the gel formed.

As a fourth example of a combinational gel would be a 1% glucan mixed with a high molecular weight carboxymethylcellulose and glycerol to a final concentration of the two latter at 1% and 20% respectively. The formulation gel can be established by adding the appropriate amount of CMC in a 1% aqueous solution of glucan. After CMC is completely dissolved, the formulation is heated to above or about 100° C. followed by the addition of glycerol. The formulation is then rapidly cooled to form a gel with the appropriate properties.

The glucan compositions of the present invention are potent therapeutic agents and in a further aspect the present invention provides the compositions as described herein for use in therapy, in particular for the treatment of conditions where a subject is in need of a systemic or local enhancement of the immune response, e.g. where there is tissue damage or infection. The compositions are of particular utility in assisting wound or ulcer healing and in the treatment of oral mucositis. They are also of utility in treating cancer or reducing tumour size.

In a further aspect the present invention provides therefore a method of assisting wound or ulcer healing or treating oral mucositis or cancer or reducing tumour size in a subject in need thereof which comprises administration to said subject of a glucan composition of the present invention as described herein.

Preferably the glucan is administered orally. preferably the glucan is administered at a dosage of 5 to 200 mg/kg/day, more preferably 20 to 100 mg/kg/day.

Reference is made to "assisting" wound or ulcer healing because some wounds or ulcers will heal naturally and others may not but the compositions of the invention have been shown to accelerate wound and ulcer healing. In some cases, healing may not occur satisfactorily without treatment. An example for such a wound which demands treatment for healing is diabetic foot ulcer. In this indication the patient develops wounds based on the underlying cause which is diabetes. Due to the often untreated underlying cause and the fact that these wounds are to be found on the feet of patients, these ulcers do not heal by themselves and cause huge problems for the patient usually ending in amputation of the foot.

Suitable pharmaceutical compositions may comprise a glucan and a gelling agent as defined above and one or more pharmaceutically acceptable diluents or carriers, preferably water and optionally one or more physiologically acceptable stabilisers or further diluents or carriers. The compositions may conveniently be formulated into any topical dosage form. The topical dosage forms may be creams, lotions, solutions, gels, ointments, pastes, sprays, films, etc. Preferably the gel composition of the invention is suitable for storage in and dispensing from a tube, e.g. a plastic tube.

In some variations, the compositions as described herein are in the form of an ointment. The ointment base may be an oleaginous base, an emulsifiable base, an emulsion base, or a water-soluble base. In other variations, the compositions according to the present invention are in the form of a cream. The creams may be viscous liquids or semisolid emulsions, either oil-in-water or water-in-oil. The cream bases may be water-washable, and contain an oil phase, an emulsifier, and an aqueous phase. In yet further variations, the compositions of the present invention are in the form of a lotion. The lotions may be formulated as suspensions of solids and contain suspending agents to produce better dispersions. The compositions according to the present invention may also be formulated pastes. Pastes are semisolid dosage forms in which the active agent is suspended in a suitable base. Depending on the nature of the base, pastes are divided between fatty pastes or those made from a single-phase aqueous gels.

In some variations, the compositions form a film on the wound surface. To aid film formation, film forming agents such as, but not limited to, acrylic acid and its derivatives, polyacrylic and its derivatives such as polybutylmethacrylate and polymethacrylic acid, polymethacrylate, ascorbyl palmitate, carbomer, carnauba wax, cellulose derivatives such as cellulose acetate phthalates, rosca mellose sodium, hydroxyethyl cellulose, hydroxypropyl cellulose, hydroxypropyl methylcellulose, ethyl cellulose and related compounds, hydroxypropyl methylcellulose phthalate, hypromellose phthalate, cetyl alcohol and derivatives, microcystalline wax, poloxamer, polyethylene glycol, polyurethane, polyvinyl acetate, polyvinyl acetate phthalate, polyvinyl alcohol, silicone rubber and derivatives, shellac, triglycerides derivatives, and combinations thereof are used.

The compositions can also include at least one film plasticizer agent that may serve to soften the polymer film formed by the film forming agent so that it is sufficiently flexible to move with area of the body applied without cracking or peeling.

In some variations, the compositions may be cast into a film prior to application to the wound or applied to the wound directly where they polymerize in situ. A "spread-on" film polymerizes when applied to the skin and may be delivered as a cream or ointment from a tube, roll-on, spray, and the like. The film may be created by incorporating a silicone rubber, into the external phase. Upon mixing with the internal phase, the resultant emulsion is allowed to cure and provides a "spread-on" film, which polymerizes when applied to the wound. The emulsion may be spread onto a substrate to achieve a desired thickness.

In other instances, the compositions may be preformed into a layer or patch. The patch may be of varying thickness. The patch may also be cut to have a shape that generally follows the wound edges.

In some variations, the patches may include a pharmaceutically acceptable adhesive material that serves to affix the patch to the wound or skin. A patch backing layer may also be included.

The compositions may be directly placed on a wound, or placed on a substrate for application on a wound. Any substrate (carrier) may be used with compositions described here. For example, woven, non-woven, knitted, foam, and adhesive substrates may be used. Absorbent or non-absorbent substrates may also be used. In some variations, the compositions are sprinkled or spread on the substrate. In other variations, the compositions are impregnated within the substrate.

The wound dressings may be applied for any suitable time period. For example, they may be applied over a time period of one day, over several days, over several weeks, or for several months or more. In general, the wound dressings will be reapplied until the wound is healed. The duration of wound treatment with the dressings described here may depend on such factors as the type of wound being treated, wound location, and form of the composition being applied. Depending on the form used, the composition may be removed with water, or wiped or peeled off the wound.

The compositions described here may be used to treat wounds resulting from any etiology. For example, the wounds may be due to burns, infections, ischemia, lymphedema, neoplasms, neuropathy, radiation damage, surgical procedures, venous insufficiency, and trauma. The compositions of the present invention are of particular utility in assisting wound or ulcer healing.

The invention further provides a physical support, for example any medical device or material for medical use having applied thereto, including impregnated therein, a composition of the invention as defined herein.

One important characteristic of the glucans of these compositions is their water holding capacity and gel formation characteristics even in the absence of conditions like non-neutral pH or cations which might promote gel healing. Some beta-glucans would form gels at concentrations as low as 1%, but more typically in the range of 2-4%. A soluble beta-glucan from yeast like the preferred glucans described herein will form a thixotropic and pseudoplastic gel when dissolved in aqueous solution at a concentration of 1-6% in pH range from 3-7, independent of the presence of cations.

Encompassed by the terms 'wound' and 'ulcer' are surface wounds, surgical wounds, burns, open fractures, leg ulcers, apthous ulcers, diabetic ulcers and decubitus ulcers. Wounds may be as a result of injury, surgery or disease but all are characterised by a loss of dermal integrity, the skin may be torn, cut or punctured and regrowth of the skin is required to seal the opening. The compositions of the present invention have been shown to accelerate wound closure. As shown in the Examples, efficacy can readily be demonstrated by measuring the size of an open wound.

The compositions are preferably applied topically, e.g. as a gel, transdermal patch, lotion, ointment, cream etc. Compositions may be applied daily, more frequently or less frequently, e.g. twice daily or on alternate days and for a duration as determined by a clinician or in some cases by the patient or other health advisor. The duration of treatment will depend on the nature and severity of the wound or ulcer with progress generally being readily determined by visual inspection.

Topical administration includes administration in the mouth and suitable, gels, lozenges, pastes, sprays etc. for delivery to the oral mucosa are known in the art.

The compositions find utility in human and veterinary medicine. As used herein, the term 'medical' includes veterinary applications and contexts. Humans are preferred subjects for treatment but other animals which may usefully be treated include livestock and companion animals.

The compositions of the invention may be applied to or incorporated in a physical/solid support such as a patch, dressing, plaster, bandage, film, gauze etc. which can be applied to the wound or ulcer site and such products constitute a further aspect of the present invention.

It will be appreciated that preferred features applicable to one aspect or embodiment of the invention apply, mutatis mutandis, to all aspects and embodiments.

In general, the wound is irrigated with normal saline or sterile water and debridement of necrotic tissue and callous completed. A composition according to the present invention is then applied to the wound. The form of the composition may depend on such factors as the surface area of the wound to be covered, type of wound being treated, and location of the wound. For example, a composition in the form of a gel, cream, or ointment may be useful for ulcers and burns, while gauze impregnated with a solution of the composition according to this invention may be useful for surgical or traumatic wounds.

The composition of the present invention may be in the form of kits. The kits described here may include one or more of the compositions of the invention and instructions for use. One or more substrates may optionally be included. In some instances, an applicator for spreading the compositions may also be provided. The compositions included in the kits may have the same topical form or different topical forms. The same or different amounts of the compositions may also be employed. Substrates may also have the same or different form. The substrates may also be of varying shape and thickness.

The invention will now be further described in the following non-limiting Examples and figures in which:

FIG. 1 illustrates the SEC-MALS-RI chromatograms of a number of batches of preferred yeast glucans, defined as branched β(1,3) glucan with <2% repetitive β(1,6) linked glucosyl units, analyzed in DMAc/with 0.5% LiCl assuming a dn/dc=0.12. As can be seen the molecular weight distribution is in the range of approx. 10,000 g/mol to approx. 200,000 g/mol on the single chain level.

FIG. 2 shows SEC-MALS-RI chromatograms of a number of batches of preferred yeast glucans, defined as branched β(1,3) glucan with <2% repetitive β(1,6) linked glucosyl units, analyzed in aqueous buffer (0.1M $NaNO_3$) assuming a dn/dc=0.15. As can be seen the molecular weight distribution is in the range of approx. 10,000 g/mol to above 10,000,000 g/mol on the single chain level. The aqueous SEC-MALS-RI results, in combination with the results in DMAc/LiCl, show that the preferred yeast glucans exist as aggregates/supramolecular structures in the aqueous solution.

FIG. 3: shows the assumed mechanism of action of the soluble beta glucan used in the present invention. The figure shows that the beta glucan (BG) branches simultaneously bind to receptors on e.g. macrophages and thus activate the innate immune system.

Figure 8:
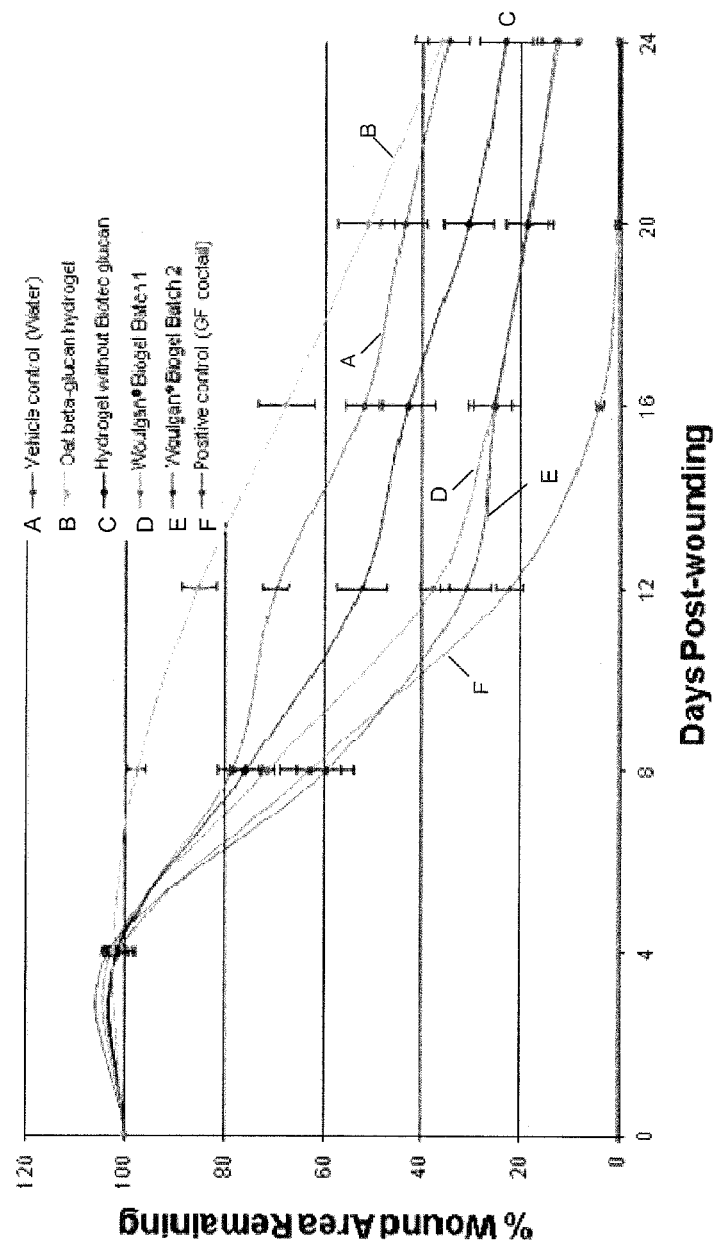
Figure 9:
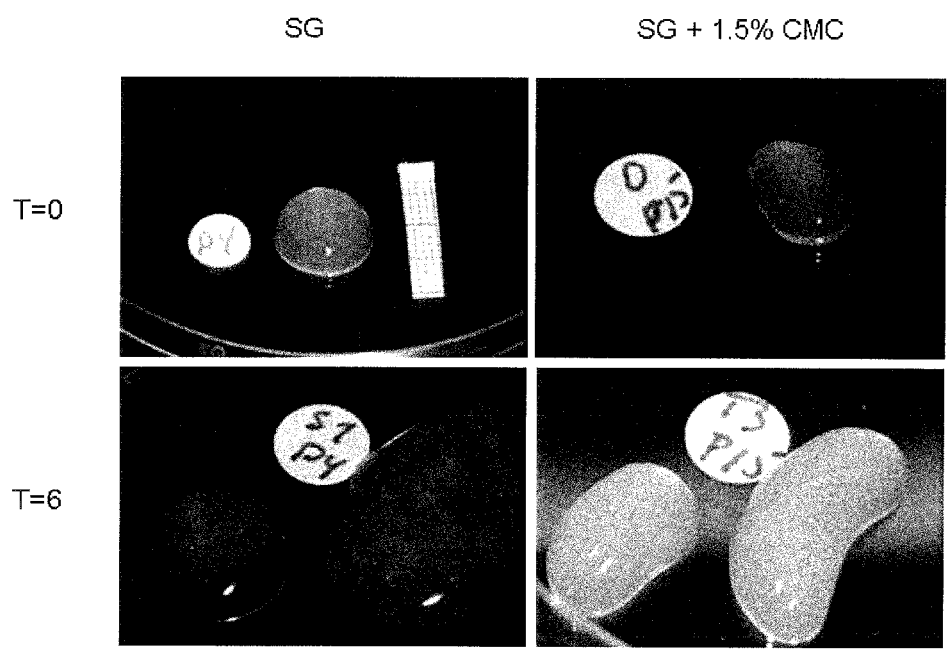

FIG. 8 shows wound closure of full-thickness wounds in a db/db mouse model stimulated by topical administration of two different formulations of Biotec Pharmacon's Woulgan Biogel, the hydrogel alone, an oat beta-glucan product, versus vehicle (water) and positive control (rh-PDGF-BB (10 μg)+rh-TGF-α (1 μg) in hydrogel FIG. 9 shows SG and SG mixed with 1.5% carboxymethylcellulose stored in aluminium containers. T=0 represents appearance at study start, and T=6 indicates samples stored 6 months at ambulating temperatures, changing each week between 4 and 37° C.

EXAMPLES

Example 1: Preparation of Gel Glucan Product (SG)

An aqueous solution of 1.5-2% yeast glucan molecules was treated as described below. This aqueous solution was prepared from a particulate glucan preparation by formolysis to selectively remove β-1,6 side chains and subsequent purification and diafiltration to remove particulate matter and low molecular weight components from the formolysis solution. A suitable formolysis step is disclosed in Example 3 of EP 0759089 B1. The particulate glucan was itself prepared from cell walls of Baker's Yeast (*S. cerevisiae*) by separate extractions with alkali, ethanol and water, each extraction being followed by appropriate drying (spray drying and vacuum drying).

a. Heat Treatment:

Heat treatment takes place after the concentration of the glucan solution has been adjusted, normally giving a product volume of approximately 220 liters at a temperature of approximately 60° C., in a closed and agitated 800 liter tank which is heated by introduction of steam to a jacket surrounding the tank.

The product is heated slowly to approximately 105° C. to ensure an even heating of the whole batch, and then more quickly to 123° C. Normal heating time from 60 to 123° C. is 40-50 minutes. The product is then held at 123-125° C. for 20 minutes.

b. Active Cooling:

Active cooling is then started. It is operated manually, by direct opening and closing of hand operated valves. First the steam is carefully evacuated from the jacket to drain, and the drain valves are left open. Cooling water is then carefully introduced to the jacket, slowly at first to avoid excessive thermal stress to the steel of the tank. As the temperature drops the flow of water is increased. Cooling is normally continued until the product temperature reaches 35-40° C. Normal cooling time from 123 to 40° C. is 50-60 minutes.

Example 2: Preparation of Gel Glucan Product

An aqueous solution of 1.5-2% yeast glucan molecules was treated as described below. This aqueous solution was prepared from a particulate glucan preparation by formolysis to selectively remove β-1,6 side chains, as described in Example 1.

a. Disruption of Hydrogen Bonds by Addition of Sodium Hydroxide:

Addition of sodium hydroxide took place after the concentration of the glucan solution had been adjusted, giving a product volume of approximately 185 liters in a closed and agitated 800 liter tank which is heated or cooled by introduction of steam or water to a jacket surrounding the tank.

The product was cooled to 18° C., and 24 moles (960 g) of NaOH, dissolved in approximately 10 liters of purified water, was poured slowly (approximately 1 liter per minute) through a hatch in the tank.

b. Restoration of Hydrogen Bonds by Addition of Hydrochloric Acid:

The restoration process was started immediately after the last of the NaOH had been poured into the tank.

Slightly less than 24 moles of HCl, approx 9 liters of 2.4 M HCl solution in purified water, was poured into the tank relatively quickly (in approximately 2 minutes), the pH of the product was measured, and more acid added in small portions until pH reached approximately 4. Total amount of HCl added was 23.4 moles.

c. Removal of Salt

To remove the ions ($Na^+$ and $Cl^-$) added during steps a and b, the product was diafiltered over a tangential filter against 4 volumes of purified water.

Example 3: Wound Healing Composition In Vivo

The impact of a gel glucan alone (SG) prepared in accordance with Example 1, vehicle (carboxymethyl cellulose or gellan gum) alone, or a combination of SG and vehicle on wound healing was investigated by analysing the repair of full-thickness excisional skin wounds in the diabetic (db/db) mouse model (i.e. BKS.Cg-m $Dock7^m$+/+ $Lepr^{db}$/J mice). The combination product of the invention was also prepared in accordance with heating and rapid cooling method described herein and exemplified in Example 1, in short, the glucan and vehicle were dissolved in aqueous solution and then heated in an autoclave to around 120° C. for about 18 minutes. The product was then cooled quickly to allow gel formation as described in Example 1.

Upon acclimatization (5-7 days without disturbance) the animals were housed in groups of 5 animals according to Home Office regulations and the specific requirements of diabetic animals. After experimental wounding, animals were housed in individual cages (cage dimensions 35×15× 15 cm with sawdust bedding, changed twice weekly), in an environment maintained at an ambient temperature of 23° C. with 12-hour light/dark cycles. The mice were provided with food (Standard Rodent Diet) and water ad libitum. Following all anaesthetic events, animals were placed in a warm environment and monitored until they were fully recovered from the procedure. All animals received appropriate analgesia (buprenorphine) after surgery and additional analgesics as required. All animal procedures were carried out in a Home Office licensed establishment under Home Office Licences (PCD: 50/2505; PPL: 40/3300; PIL: 50/3482; PIL: 70/4934). The health of animals was monitored on a daily basis throughout the study.

On day 0, animals were anaesthetised (isofluorane & air) and the dorsum shaved and cleaned with saline-soaked gauze. A single standardised full-thickness wound (10.0 mm×10.0 mm) was created in the left dorsal flank skin of each experimental animal. Wounds in all treatment groups were subsequently dressed with a circumferential band of the transparent film dressing Bioclusive™ (Systagenix Wound Management, UK); after which they received either SG, vehicle, or a combination of SG and vehicle by injection 50 µl material dissolved in purified water through the Bioclusive film using a 29-gauge needle. Diabetic animals were randomized to one of the treatment regimes using appropriate software.

Treatments were reapplied on post-wounding days 2, 4 and 6. Wound sites in these animals were closely monitored for excessive build-up of applied agents and excessive wound site hydration; if excessive applied agent accumulation/hydration was apparent, previously applied material was removed by aspiration prior to reapplication.

On post-wounding days 4, 8, 12, 16, 20 and 24 all animals were re-anaesthetised, their film dressings and any free debris removed, and their wounds cleaned using saline-soaked sterile gauze. After photography on days 4, 8, 12, 16, 20 and 24 wounds were re-dressed as above with Bioclusive film dressing. Wound healing was evaluated (not quantitatively) according to the presence of fibrin, granulation tissue, angiogenesis and re-epitelisation. Based on appearance of the above mentioned factors neo-dermal tissue formation (healing) were classified as: Very good, good, slight, no.

Wound closure data were further determined from scaled wound images taken of each wound at each assessment point. The area of a given wound, at a given time point, was expressed as a percentage of the area of that wound immediately after injury (i.e. day 0). The mean percentage wound area remaining (& standard error of mean) was calculated for each group and was displayed graphically. The impact of each glucan preparation was compared to that of wounds in receipt of: i). vehicle; and ii) PDGF-BB+TGF-α (positive control).

TABLE 1

Fraction of healing wounds, day 8.

| Treatment | Healing (neo-dermal tissue formation) | | | |
|---|---|---|---|---|
| | Very good | Good | Slight | No |
| 1% Carboxymethyl cellulose | 0/10 | 3/10 | 2/10 | 5/10 |
| 2% SG | 0/10 | 5/10 | 4/10 | 1/10 |
| 4% SG | 2/10 | 4/10 | 3/10 | 1/10 |
| 1% Carboxymethyl cellulose + 1% SG | 0/10 | 5/10 | 4/10 | 1/10 |
| 1% Carboxymethyl cellulose + 2% SG | 3/10 | 5/10 | 2/10 | 0/5 |
| 1% Carboxymethyl cellulose + 4% SG | 1/10 | 9/10 | 0/5 | 0/5 |
| 0.3% Phytagel | 0/10 | 5/10 | 3/10 | 2/10 |
| 0.3% Phytagel + 2% SG | 0/10 | 8/10 | 2/10 | 0/10 |

The results in Table 1 show that the frequency of healing wounds in receipt of the glucan alone was higher relative to wounds in receipt of the vehicle alone. This suggests that the glucan alone is a better inducer of neo-dermal tissue formation compared to the gelling agent (the vehicle). In addition, there is a clear concentration-dependent shift from a 2% to a 4% glucan solution showing increase wound healing (good to very good). However, the combination of the glucan and both of the vehicles was superior to the single use of each agent (significant shift from slight to good and very good), suggesting a synergistic effect of the combined products.

Example 4: The Impact of Glucan Preparations According to the Invention on Wound Healing A study was performed to evaluate glucan-based preparations according to the invention with regard to their ability to promote tissue repair in a recognised in vivo model of delayed wound healing. Patients with diabetes are prone to impaired wound healing, with foot ulceration being particularly prevalent. This delay in wound healing also extends to diabetic animals, including the spontaneously diabetic (db/db) mouse (i.e. BKS.Cg-m $Dock7^m$+/+$Lepr^{db}$/J mice).

In this study, the healing of wounds on diabetic mice in receipt of Biotec glucan SG 131-9 (at various concentrations, with or without various vehicles) was compared to that of similar wounds exposed to the vehicles: (i) purified water [water for injection], (ii) 1.0% carboxy-methyl-cellulose, and (iii) 0.3% Phytagel. The healing of diabetic wounds in receipt of Biotech glucan SG 131-9 was also compared to the comparators: (i) Methocel—a comparator polysaccharide material, and (ii) Intrasite Gel—a market leading wound management hydrogel preparation. Recombinant human platelet-derived growth factor-BB (rh-PDGF-BB) in combination with recombinant human Transforming Growth Factor-alpha (rh-TGF-α) were used as the "positive control" in this study. This positive control was applied with two carriers—0.5% hydroxy propyl methyl cellulose (HPMC) and 1.0% carboxy methyl cellulose (CMC).

Materials and Methods
Materials Under Test
 1. Water for Injection
 2. 1.0% Carboxymethylcellulose (CMC, Sigma C5013, sodium salt) in purified water
 3. 0.3% Phytagel+4 mM $CaCl_2$
 4. 2.0% Methocel
 5. Intrasite
 6. 2.0% SG
 7. 4.0% SG
 8. 1.0% CMC+1.0% SG
 9. 1.0% CMC+2.0% SG
 10. 1.0% CMC+4.0% SG
 11. 0.3% Phytagel+2.0% SG
 12. rh-PDGF-BB [10%]+rh-TGF-α [1%]—in 0.5% HPMC
 13. rh-PDGF-BB [10%]+rh-TGF-α [1%]—in 1.0% CMC The above materials were prepared in accordance with the methods described in Examples 1 and 3. Phytagel is always used with $CaCl_2$.

BKS.Cg-m Dock7$^m$+/+Lepr$^{db}$/J Diabetic Mouse Model

Mice were brought into the UK aged approximately 5-6 weeks and maintained 'in house' until aged 12 weeks (±1 week)—according to Home Office regulations and the specific requirements of diabetic animals.

Briefly, on day 0 mice were anaesthetised using isofluorane and air; and their dorsal flank skin was clipped and cleansed according to protocol. A single standardised full-thickness wound (10 mm×10 mm) was created in the skin immediately to the left of the spine. Diabetic animals were randomly allocated to one of 13 experimental groups (as described in the table below). Wounds in all groups were dressed with a circumferential band of the semi-occlusive film dressing Bioclusive™ (Systagenix Wound Management, UK) and treatments (in 50 μl volumes [groups 1-11] and 100 μl [groups 12 &13]) applied by hypodermic injection through the Bioclusive film. The condition of dressing materials was examined daily throughout the study and replaced as necessary.

Animals in groups 1 through 11 were restrained and treatments reapplied by hypodermic injection through the Bioclusive film on post-wounding days 2, 4 and 6. Any build-up of hydration/previously applied agent was removed by aspiration prior to re-application. For experimental groups 12 & 13 (positive controls) treatments were reapplied daily until post-wounding day 6.

On day 4 all animals were re-anaesthetised, wounds were photographed, and animals were allowed to recover in a warmed environment (34° C.). As wound boundaries were clearly visible through the Bioclusive™ dressing, and in order to minimise peri-wound damage through repeated dressing removal, it was decided that the film dressings would be retained at this assessment point.

On days 8 & 12, 16 & 20 all animals were re-anaesthetised, their film dressings and any free debris removed, and their wounds cleaned using sterile saline-soaked sterile gauze. Wounds were then photographed, re-dressed (as above) with Bioclusive™ film dressing—and animals were allowed to recover in a warmed environment (34° C.).

Immediately after wounding, and subsequently on days 4, 8, 12, 16, 20 & 24 all wounds were digitally photographed together with a calibration/identity plate (following film dressing removal and wound cleaning—where applicable).

Experimental Groups:

| Tx Group | Treatment | Group name | Animal Codes & harvesting | "n" |
|---|---|---|---|---|
| 1 | Water for Injection | EXP-01 | BIOT-02.01 to 02.10 | 10 |
| 2 | 1.0% Carboxymethylcellulose(CMC) in purified water (50 μl) | EXP-02 | BIOT-02.11 to 02.20 | 10 |
| 3 | 0.3% Phytagel + 4 mMCaCl$_2$(50 μl) | EXP-03 | BIOT-02.21 to 02.30 | 10 |
| 4 | 2.0% Methocel (50 μl) | EXP-04 | BIOT-02.31 to 02.40 | 10 |
| 5 | Intrasite (50 μl) | EXP-05 | BIOT-02.41 to 02.50 | 10 |
| 6 | 2.0% SG (50 μl) | EXP-06 | BIOT-02.51 to 02.60 | 10 |
| 7 | 4.0% SG (50 μl) | EXP-07 | BIOT-02.61 to 02.70 | 10 |
| 8 | 1.0% CMC + 1.0% SG (50 μl) | EXP-08 | BIOT-02.71 to 02.80 | 10 |
| 9 | 1.0% CMC + 2.0% SG (50 μl) | EXP-09 | BIOT-02.81 to 02.90 | 10 |
| 10 | 1.0% CMC + 4.0% SG (50 μl) | EXP-10 | BIOT-02.91 to 02.100 | 10 |
| 11 | 0.3% Phytagel + 2.0% SG (50 μl) | EXP-11 | BIOT-02.101 to 02.110 | 10 |
| 12 | rh-PDGF-BB [10 μg] + rh-TGF-α [1ug]-(100 ul) in 0.5% HPMC | EXP-12 | BIOT-02.111 to 02.117 | 7 |
| 13 | rh-PDGF-BB [10 μg] + rh-TGF-α [1ug]-(100 ul) in 1.0% CMC | EXP-13 | BIOT-02.118 to 02.124 | 7 |

Image Analysis of Wound Closure:

Image Pro Plus image analysis software (version 4.1.0.0, Media Cybernetics, USA) was used to calculate wound closure from scaled wound images taken at each assessment point. As the process of wound closure involves the effects of wound contraction (the inward movement of marginal tissue), this was also determined The following assessments were made:
1. Percentage wound area remaining with time i.e. the open wound area remaining at a given time point—relative to the area of the same wound immediately after injury on day 0.

2. Percentage wound contraction with time
   i.e. the difference between the contracted wound area at a given time point and the original wound area [as a percentage of the original wound area.

Assessment of Initiation of Wound Healing (Neo-Dermal Tissue Generation):

All wounds in the study were visually assessed on a daily basis until day 8—and subsequently on days 10, 12, 14, 16, 20 & 24 to establish their "healing" status. Each wound was scored as to whether it was displaying "neo-dermal tissue generation activity" or not (i.e. whether the wound had initiated the healing process or not). Each wound was assessed by two independent observers and the average percentage of wounds displaying "neo-dermal tissue generation activity" was compared between treatment groups at each assessment point.

Neo-dermal tissue formation was considered to have initiated when blood vessels within the fascia of the wound base are concealed by overlying "material". This concealment may result from the formation of cloudy exudate, polymerised/semi-polymerised fibrin or granulation tissue. Invariably, the first sign of neo-dermal tissue initiation is the formation of a reddish exudate within the wound void.

Results

Wound Closure:

For a given wound at a given time point, wound closure was expressed as the percentage wound area remaining relative to the initial wound area immediately after injury (i.e. day 0). Mean percentage wound area remaining data for all treatment groups are described in Table 2, below.

Application of SG 131-9 (1, 2 or 4%) in CMC tended to accelerate wound closure compared to water treatment. Treatment with 1% SG 131-9 (in CMC) resulted in significantly elevated closure on post-wounding days 12 through 20. Treatment with 2% SG 131-9 (in CMC) appeared to lead to more substantial and sustained effects and was found to result in a significant acceleration in closure from day 12 onwards. Treatment with 4% SG 131-9 (in CMC) though more effective than water, appeared less effective than both the 1% and 2% treatments. The final wound closure levels reached by day 24 were: 90% for 1% SG 131-9 (in CMC), 96% for 2% SG 131-9 (in CMC) and 89% for 4% SG 131-9 (in CMC).

2% SG 131-9 applied in 1% CMC tended to elevate wound closure to a greater degree than 2% SG 131-9 applied in water. When the three 2% SG 131-9 treatment regimes are compared, it can be seen that all three promoted closure to a greater level than their respective vehicle controls (i.e. water, 1% CMC & 0.3% Phytagel). In absolute terms, 2% SG in CMC tended to result in the highest level of closure. The closure profile of the 2% SG in water treatment group was similar to that of the 2% SG in Phytagel treatment group, both displayed lower levels of closure than wounds treated with the 2% SG 131-9 in CMC formulation.

Of all the SG 131-9 preparations evaluated, 2% SG 131-9 in 1% CMC appeared to be most effective. 2% SG 131-9 (in CMC) was found to promote wound closure to a greater degree than Intrasite, a comparator polysaccharide material and Methocel, a market leading wound management hydrogel preparation.

Wound Contraction

Contraction is the centripetal movement of the wound margins—due to the compaction of granulation tissue within

TABLE 2

Percentage "Wound Area Remaining" Data for all study groups.

| | | % wound area remaining with time - open wound area (mean +/− standard error) | | | | | |
|---|---|---|---|---|---|---|---|
| | Days post-wounding | 4 | 8 | 12 | 16 | 20 | 24 |
| Treatment | (1) Vehicle - purified water | 96.7 ± 2.8 | 70.1 ± 2.9 | 60.6 ± 4.7 | 41.0 ± 6.3 | 30.8 ± 5.8 | 22.9 ± 5.6 |
| | (2) Vehicle - 1% CMC | 97.5 ± 1.9 | 66.9 ± 4.2 | 42.3 ± 4.5 | 21.9 ± 4.3 | 12.9 ± 3.4 | 6.1 ± 1.7 |
| | (3) Vehicle - 0.3% Phytagel + 4 mM $CaCl_2$ | 95.2 ± 3.4 | 70.4 ± 4.4 | 49.2 ± 5.1 | 34.0 ± 6.2 | 21.6 ± 5.9 | 12.9 ± 5.3 |
| | (4) 2.0% Methocel | 99.0 ± 2.2 | 58.3 ± 5.5 | 44.4 ± 6.2 | 28.2 ± 7.3 | 16.4 ± 5.8 | 9.3 ± 4.1 |
| | (5) Intrasite | 95.2 ± 2.2 | 74.4 ± 4.4 | 49.1 ± 5.0 | 28.0 ± 4.6 | 15.0 ± 3.9 | 7.8 ± 2.8 |
| | (6) 2.0% SG | 93.2 ± 2.8 | 63.7 ± 3.8 | 37.5 ± 5.0 | 19.9 ± 3.4 | 13.1 ± 4.6 | 8.7 ± 4.3 |
| | (7) 4.0% SG | 100.2 ± 4.4 | 64.5 ± 4.7 | 39.6 ± 5.7 | 25.6 ± 5.0 | 20.3 ± 4.7 | 15.7 ± 5.2 |
| | (8) 1.0% SG 131-9 (in 1% CMC) | 97.8 ± 2.7 | 68.8 ± 2.8 | 37.4 ± 5.0 | 19.2 ± 4.0 | 14.9 ± 4.0 | 10.2 ± 3.9 |
| | (9) 2.0% SG 131-9 (in 1% CMC) | 98.1 ± 3.0 | 60.2 ± 6.5 | 31.3 ± 6.2 | 15.0 ± 3.6 | 7.7 ± 2.3 | 3.9 ± 1.6 |
| | (10) 4.0% SG 131-9 (in 1% CMC) | 97.2 ± 2.8 | 66.6 ± 4.5 | 53.5 ± 5.5 | 30.4 ± 3.9 | 18.9 ± 3.7 | 11.2 ± 2.5 |
| | (11) 2.0% SG 131-9 (in 0.3% Phytagel) | 97.0 ± 2.0 | 67.3 ± 3.0 | 38.7 ± 3.7 | 24.5 ± 3.3 | 11.2 ± 1.9 | 7.0 ± 1.7 |
| | (12) Positive control (in 0.5% HPMC) | 93.7 ± 3.2 | 58.0 ± 6.2 | 17.9 ± 3.9 | 4.8 ± 2.2 | 0.04 ± 0.04 | 0.0 ± 0.0 |
| | (13) Positive control (in 1.0% CMC) | 91.2 ± 2.4 | 57.3 ± 1.9 | 22.2 ± 3.3 | 6.2 ± 2.3 | 1.8 ± 1.2 | 0.9 ± 0.9 |

Figure 3:
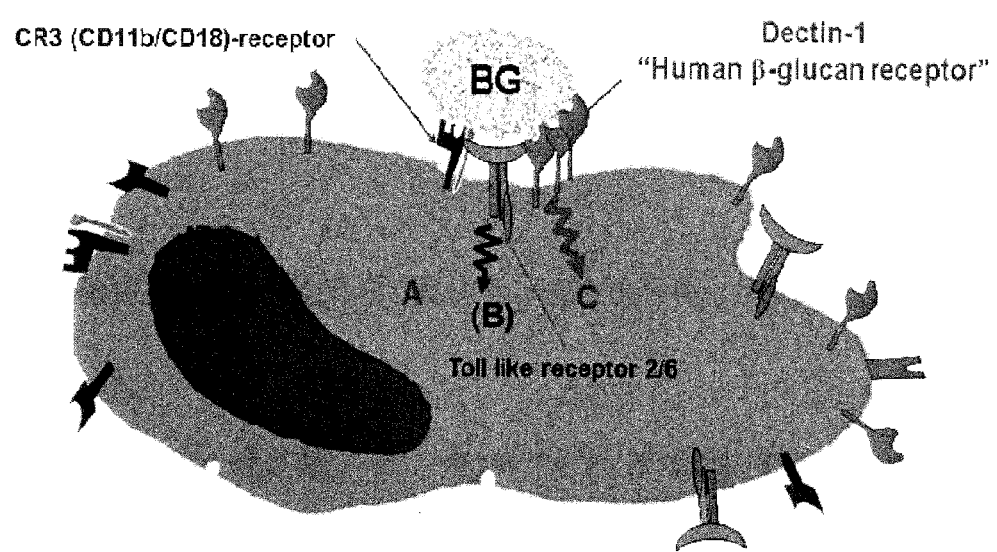
Figure 4:
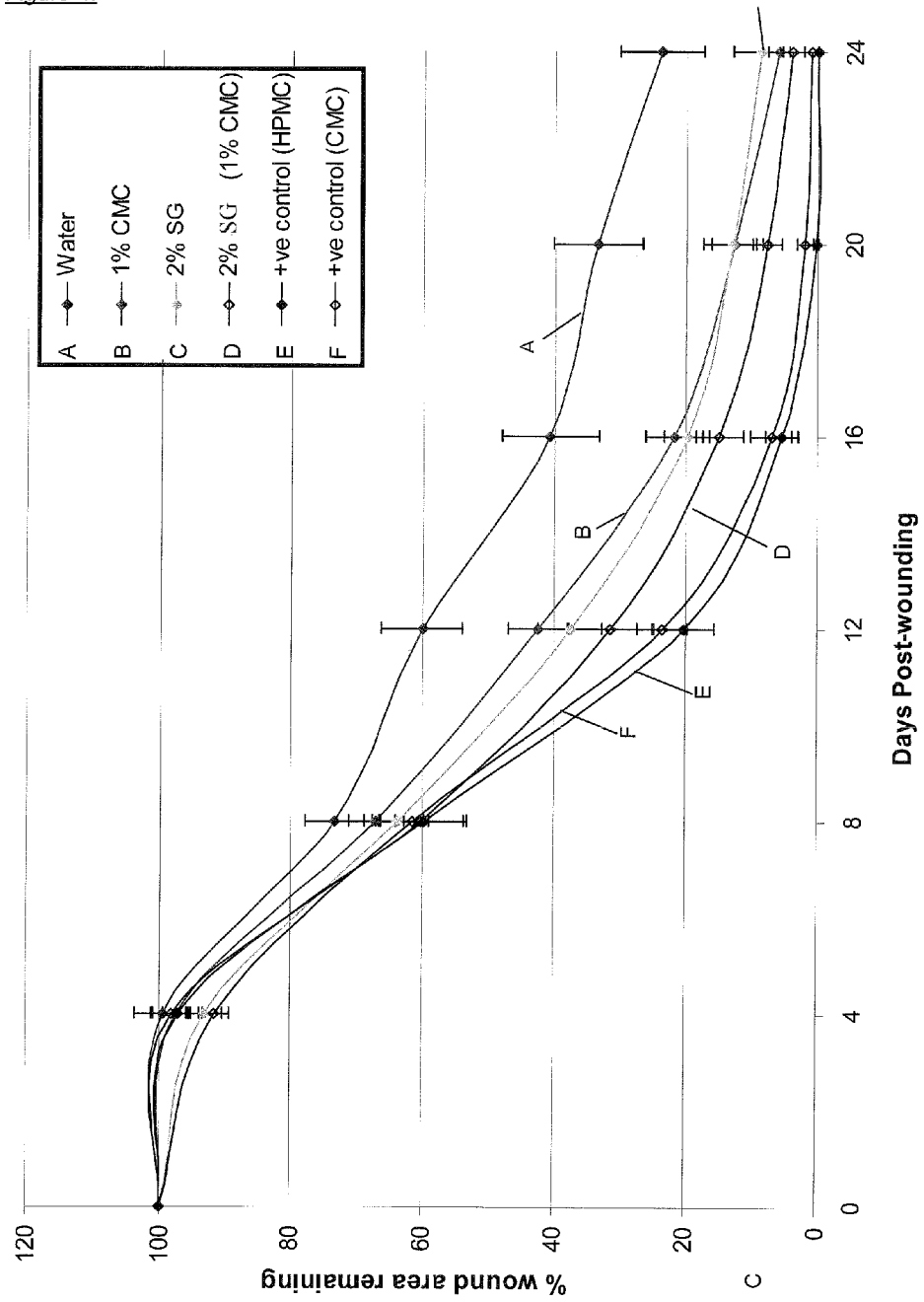
FIG. 4 shows wound closure of full-thickness wounds in a db/db mouse model stimulated by topical administration of SG alone (2%), carboxymethyl cellulose alone (1% CMC), the combination of the two (2% SG, 1% CMC), versus vehicle (water) and positive control (rh-PDGF-BB (10 μg)+rh-TGF-α (1 μg) in 0.5% HPMC and 1% CMC.
Figure 5:
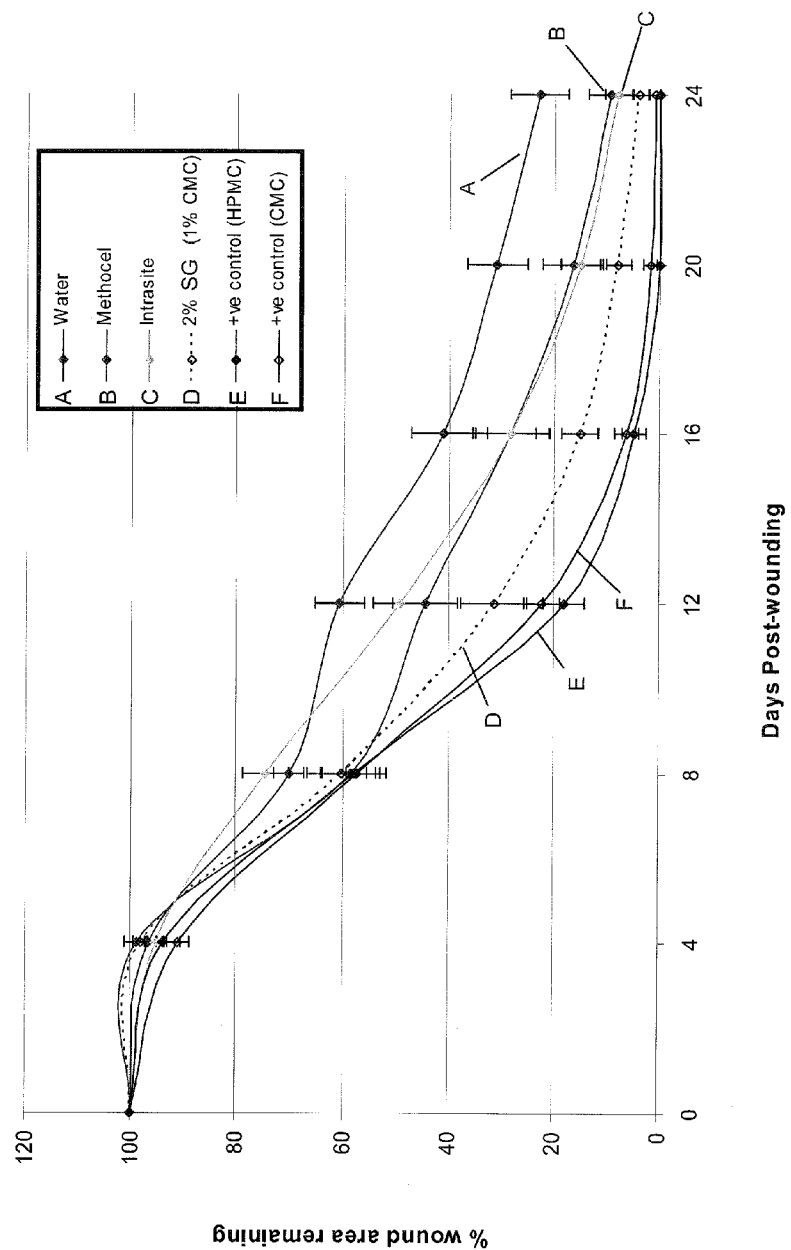
FIG. 5 shows the change in mean % wound area remaining with time (±sem)—Groups: (1) Vehicle control, (4) Methocel, (5) Intrasite, (9) 2% SG (1% CMC), (12) +ve control (HPMC), & (13) +ve control (CMC)

As shown in Table 2, and in FIGS. 4 and 5, wound closure profiles of "% wound area remaining with time" data, were found to differ noticeably between the different treatment groups. Wounds in receipt of water only demonstrated the slowest wound closure and wounds in receipt of the positive controls exhibited the fastest closure, with all other treatment groups falling between. Wounds in receipt of 2% SG (in CMC) were found to close more rapidly than any other experimental treatment group (excluding positive controls).

Both comparators (Methocel and Intrasite) tended to accelerate wound closure compared to water treatment. The final wound closure levels attained by day 24 were ~91% for Methocel and ~92% for Intrasite.

the "body" of the wound. The "compactional" forces, that drive this process, are thought to reside in cells of the fibroblast lineage. In this study, % contraction was calculated as:

$$\% \text{ contraction} = \frac{\text{The area defined by the boundary of normal}}{\text{The original wound area (day 0)}} \times 100$$

Figure 6:
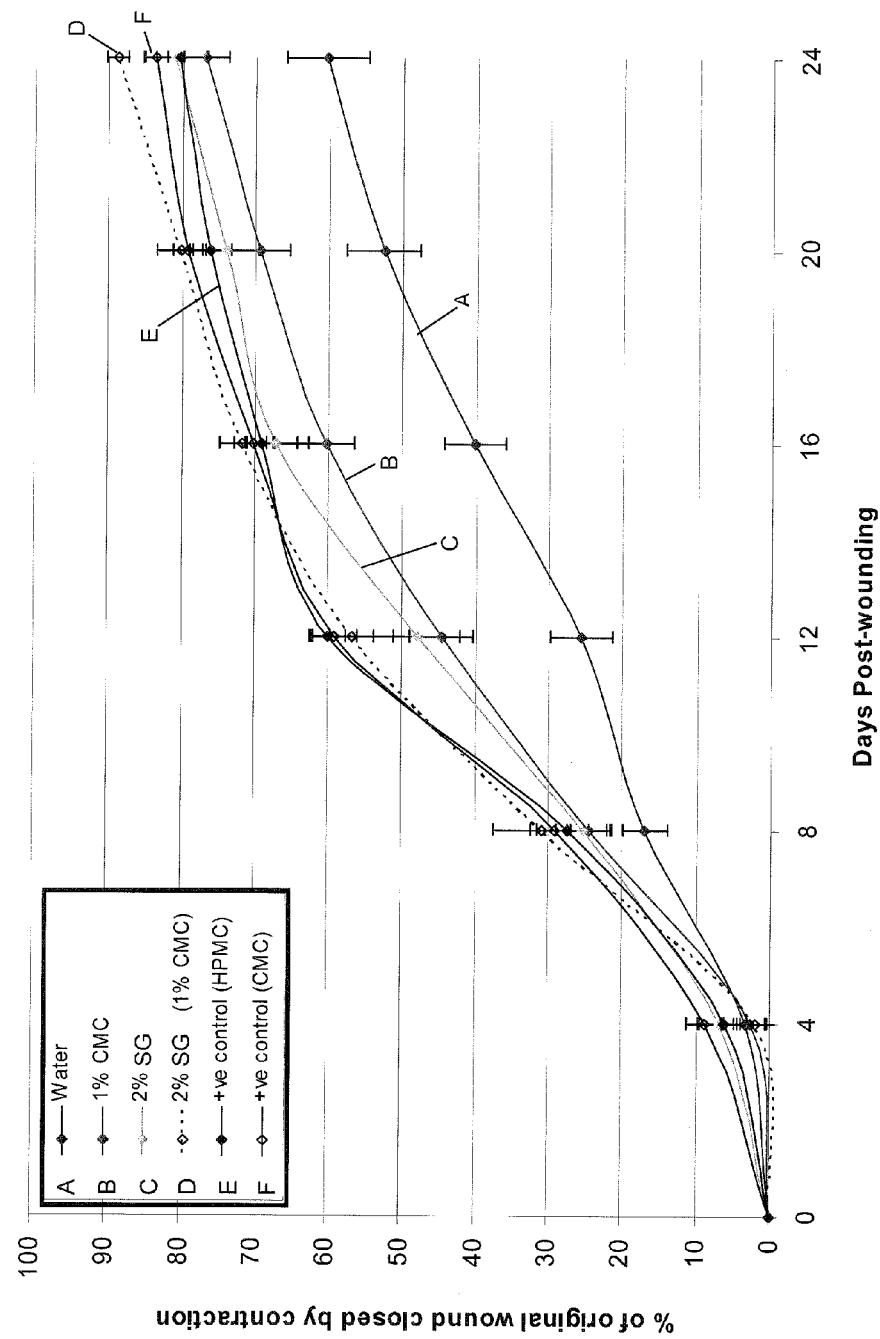
FIG. 6 shows change in mean % of original wound area closed by contraction with time (±sem)—Groups: (1) Vehicle control, (2) 1% CMC, (6) 2% SG, (9) 2% SG (1% CMC), (12) +ve control (HPMC), & (13) +ve control (CMC)
Figure 7:
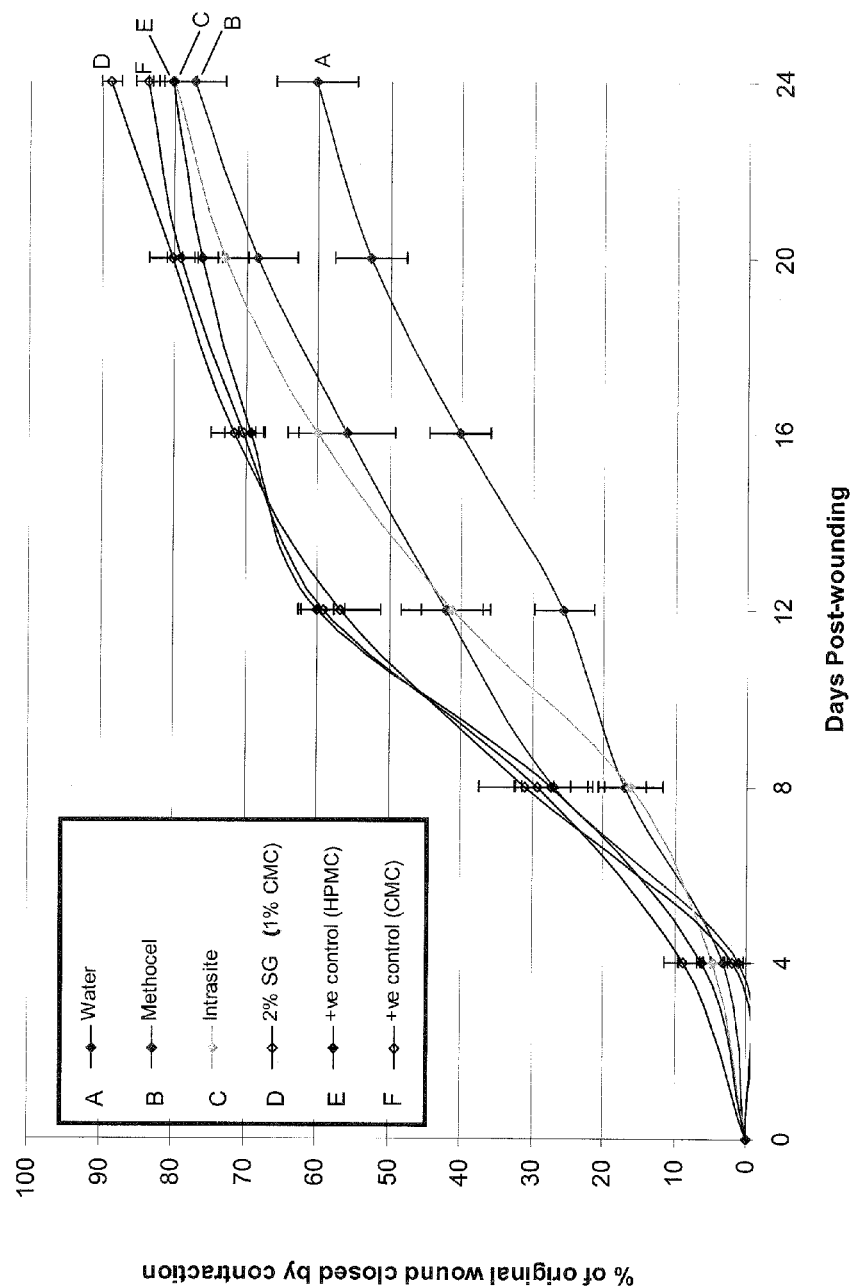
FIG. 7 shows the change in mean % of original wound area closed by contraction with time (±sem)—Groups: (1) Vehicle control, (4) Methocel, (5) Intrasite, (9) 2% SG (CMC), (12) +ve control (HPMC), & (13) +ve control (CMC)

The wound contraction results are shown in Table 3 below and FIGS. 6 and 7.

TABLE 3

| | | % of original wound area closed by contraction (mean +/− standard error) | | | | | |
|---|---|---|---|---|---|---|---|
| | Days post-wounding | 4 | 8 | 12 | 16 | 20 | 24 |
| Treatment | (1) Vehicle - purified water | 3.3 ± 2.8 | 16.9 ± 2.9 | 25.5 ± 4.2 | 40.2 ± 4.2 | 52.6 ± 4.9 | 60.2 ± 5.5 |
| | (2) Vehicle - 1% CMC | 2.5 ± 1.9 | 24.4 ± 2.9 | 44.7 ± 4.3 | 60.4 ± 3.9 | 69.3 ± 3.9 | 76.9 ± 3.1 |
| | (3) Vehicle - 0.3% Phytagel + 4 mM $CaCl_2$ | 4.8 ± 3.4 | 19.1 ± 4.3 | 38.4 ± 5.3 | 53.5 ± 6.5 | 64.6 ± 6.6 | 72.5 ± 6.5 |
| | (4) 2.0% Methocel | 1.0 ± 2.2 | 26.9 ± 5.4 | 42.1 ± 6.3 | 56.0 ± 6.7 | 68.4 ± 5.6 | 77.2 ± 4.3 |
| | (5) Intrasite | 4.8 ± 2.2 | 16.1 ± 4.6 | 41.3 ± 4.2 | 60.0 ± 4.0 | 72.9 ± 3.3 | 80.0 ± 2.9 |
| | (6) 2.0% SG | 6.8 ± 2.8 | 25.4 ± 3.6 | 48.0 ± 5.9 | 67.0 ± 4.3 | 74.0 ± 4.3 | 80.9 ± 4.4 |
| | (7) 4.0% SG | −0.2 ± 4.4 | 23.6 ± 4.0 | 49.7 ± 4.8 | 62.9 ± 4.5 | 72.8 ± 4.3 | 76.3 ± 5.2 |
| | (8) 1.0% SG 131-9 (in 1% CMC) | 2.2 ± 2.7 | 21.9 ± 3.0 | 45.7 ± 3.4 | 62.8 ± 4.1 | 71.4 ± 4.2 | 76.5 ± 4.0 |
| | (9) 2.0% SG 131-9 (in 1% CMC) | 1.9 ± 3.0 | 31.0 ± 6.5 | 56.7 ± 5.5 | 71.7 ± 3.2 | 80.1 ± 3.3 | 88.8 ± 1.4 |
| | (10) 4.0% SG 131-9 (in 1% CMC) | 2.8 ± 2.8 | 23.4 ± 3.4 | 41.8 ± 5.1 | 62.0 ± 3.7 | 73.7 ± 3.3 | 79.9 ± 2.9 |
| | (11) 2.0% SG 131-9 (in 0.3% Phytagel) | 3.0 ± 2.0 | 21.9 ± 3.9 | 50.1 ± 4.0 | 66.1 ± 2.9 | 79.8 ± 2.4 | 85.4 ± 2.2 |
| | (12) Positive control (in 0.5% HPMC) | 6.3 ± 3.2 | 27.3 ± 5.2 | 60.0 ± 2.4 | 69.2 ± 1.8 | 76.2 ± 2.8 | 80.3 ± 3.4 |
| | (13) Positive control (in 1.0% CMC) | 8.8 ± 2.4 | 29.2 ± 2.3 | 59.1 ± 3.1 | 70.2 ± 2.6 | 79.2 ± 2.0 | 83.7 ± 1.6 |

Noticeably less contraction was evident in the water only treatment group compared to all other treatment groups. The highest levels of contraction was observed with both positive control regimes, 2% SG (in CMC) and at the later time points (days 20 and 24) with 2% SG (in Phytagel).

Both comparators, Methocel and Intrasite, promoted wound contraction relative to water-treatment. Methocel-treated wounds contracted significantly more than those treated with water on days 8, 20 and 24, while Intrasite treated wounds displayed significantly more contraction from day 12 onwards. Both comparator treatment groups tended to display less wound contraction than positive control-treated wounds.

Treatment with SG 131-9 (1%, 2% or 4%) formulated in 1% CMC promoted wound contraction relative to water-treatment. Treatment with each of the concentrations resulted in significantly greater contraction than water treatment from day 12 onwards. 2% SG 131-9 (in CMC) was found to promote wound contraction compared to CMC alone, with significantly elevated contraction observed on days 16 and 24.2% SG (in CMC) was found to be more effective at promoting contraction than both 1% and 4% SG 131-9 (in CMC). Treatment with 2% SG (in CMC) resulted in similar levels of contraction as the positive control treated wounds up to and including day 20 with no significant differences measured between them; whereas, as previously described, CMC alone resulted in less contraction than the positive control treatments. Interestingly, at the final assessment point (day 24), wounds treated with 2% SG 131-9 (in CMC) were found to have contracted to a greater degree than those treated with both positive control treatment.

2% SG 131-9 applied in 1% CMC tended to elevate wound contraction to a greater degree than 2% SG 131-9 applied in water. In absolute terms, 2% SG in CMC tended to result in the highest level of contraction. 2% SG 131-9 (in Phytagel) was also found to promote wound contraction compared to water treatment and compared to Phytagel alone.

Of all the SG 131-9 preparations evaluated, 2% SG 131-9 in 1% CMC appeared to be most effective in terms of wound contraction. 2% SG 131-9 (in CMC) was found to promote wound contraction to a greater degree than Intrasite and Methocel.

Initiation of Wound Healing (Neo-Dermal Tissue Generation)

All wounds in the study were visually assessed on a daily basis until day 8 and subsequently on days 10, 12, 14, 16, 20 & 24 to establish their "healing" status. Each wound was scored as to whether it was displaying "neo-dermal tissue generation activity" or not (i.e. whether the wound had initiated the healing process or not). Each wound was assessed by two independent observers and the average percentage of wounds displaying "neo-dermal tissue generation activity" was compared between treatment groups at each assessment point.

Wounds in the different treatment groups were found to demonstrate the first signs of healing at varying times after wounding. According to these data the order in which the different groups were found to respond was, from fastest to slowest:

| Based on median no. days to respond | |
|---|---|
| Order | Treatment |
| 1 | +ve control (CMC), |
| | +ve control (HPMC) |
| 3 | 2% SG 131-9 (1% CMC) |
| | 4% SG 131-9 (1% CMC) |
| | 2% SG131-9 |
| | 4% SG131-9 |
| | Intrasite |
| 8 | Methocel |
| 9 | 2% SG131-9 (Phyta) |
| 10 | 1% SG131-9 (1% CMC) |
| 11 | Phytagel |
| 12 | 1% CMC |
| 13 | Water |

Seven of the ten wounds (70%) randomised to water treatment were found to have initiated neo-dermal tissue formation on conclusion of the study on day 24. All wounds in all other groups were found to have initiated neo-dermal tissue formation by this time point.

On consideration of SG formulated in 1% CMC, wounds in receipt of 2% and 4% SG tended to respond first, followed by wounds in receipt of 1% SG. When compared to water-treatment, a significantly greater number of 1% SG 131-9 treated wounds had responded on days 6 to 14, a significantly greater number in receipt of 2% SG 131-9 had responded on days 3 to 14, and a significantly greater number treated with 4% SG 131-9 had responded on days 4 to 14. No significant differences were noted between these three treatment groups and the two positive control treatment groups after day 4. In terms of the average number of days to respond all three concentrations responded significantly earlier than water-treated wounds.

Wounds in receipt of 2% SG formulated in Phytagel were found to respond earlier than wounds in receipt of Phytagel alone. When compared to control groups, significantly more wounds in receipt of 2% SG (in Phytagel) responded on days 4 to 14 than wounds in receipt of water. In terms of the average number of days to respond, 2% SG (Phytagel) responded significantly earlier than water or Phytagel alone.

Example 5: Glucan Gel Stability

Woulgan® was prepared as follows:
2.7% SBG (Biotec's soluble yeast beta glucan in purified water)
While stirring, Blanose™ (7H4XF PH, Kirsch Pharma Gmbh, pharma grade carboxymethyl cellulose) was added to a final conc. of 1.5% (w/v).
Stirred until CMC was dissolved
Glycerol (99.7%) added to a final conc. of 20%.
Sterilized in autoclave at 120° C. for 18 min
Cooled quickly and the gel allowed to solidify as described in Example 1.
and was stored in aluminium tubes under conditions which accelerate degradation (shaking with alternating temperatures of 4° C. and 37° C.) for up to six months. The SG alone, i.e. without the carboxymethyl cellulose, was prepared in accordance with Example 1 and stored under identical conditions. The starting material SBG is the same starting material as used in Example 1.

As shown in FIG. 9, degradation of the SG gel is enhanced by these storage conditions. Signs of degradation, i.e syneresis, can be visualised as early as 1 month under these conditions. After 6 months, the SG gel shows clear signs of syneresis and is described as a very soft, thin, heterogenous, lumpy, cracked, granular gel, while the gel consisting of SG with added carboxymethyl cellulose is unaltered compared to its appearance at study start and is retained a homogenous and sticky gel throughout the study, at least until 6 months. The combination products have been demonstrated as having enhanced stability as compared to SG alone.

The invention claimed is:

1. A gel composition comprising 0.1%-6% glucan derived from yeast and 0.2%-3% gelling agent, said composition having a melting point (gel to sol) above 37° C., wherein said gelling agent is a cellulose derivative.

2. The composition of claim 1 wherein the glucan and the gelling agent are present as a hydrogel.

3. The composition of claim 1 wherein the gelling agent is selected from the group consisting of carboxymethyl cellulose, methylcellulose, hydroxypropyl cellulose, hydroxyethyl cellulose, hydroxypropyl methyl cellulose and hydroxypropyl methyl cellulose phthalate.

4. The composition of claim 1, wherein the glucan is derived from *Saccharomyces cerevisiae*.

5. The composition of claim 1 wherein the glucan is a beta glucan comprising a backbone of β-(1,3)-linked glucosyl residues and side chains comprising 2 or more β-(1,3)-linked glucosyl residues, the sidechains being attached to the backbone via a β-(1,6)-linkage.

6. The composition of claim 1 wherein the glucan is essentially free of repetitive β-(1,6)-linked glucosyl residues.

7. The composition of claim 1 which comprises 0.2%-4% glucan and 0.25%-2% gelling agent.

8. The composition of claim 1 wherein the gel exists in gel form at 25° C. at pH 4 to 8.

9. The composition of claim 1 which at 25° C. has a viscosity of at least 1000 cP.

10. The composition of claim 1 which comprises about 2% glucan and about 1.5% carboxymethyl cellulose.

11. A method of assisting wound or ulcer healing or treating oral mucositis or cancer in a subject which comprises administering to said subject the composition of claim 1.

12. The method of claim 11 wherein the composition is topically applied to a subject.

13. The method of claim 11 wherein said ulcer is a diabetic ulcer.

14. A physical support having applied thereto or impregnated therein, the composition of claim 1.

15. The physical support of claim 14 selected from the group consisting of a woven, non-woven, knitted, foam or adhesive substrate.

16. A gel composition comprising 0.1%-6% glucan derived from yeast and 0.2%-3% gelling agent, wherein the gelling agent is a cellulose derivative, and wherein said gel composition is obtainable by a method which comprises:
 a) treating an aqueous solution of glucan molecules derived from yeast, to dissociate the glucan's hydrogen bonds;
 b) treating the aqueous solution to reform hydrogen bonds within the glucan;
 wherein the gelling agent is added prior to step a) or after step a) but prior to step b).

17. The method of claim 16, wherein step a) comprises heating the aqueous solution of glucan molecules, with or without gelling agent, and step b) comprises cooling the aqueous solution of glucan and gelling agent.

18. The method of claim 17, wherein the aqueous solution, with or without gelling agent, is heated to at least about 100° C.

19. The method of claim 17, wherein the mixture of glucan and gelling agent is rapidly cooled in step b).

20. The method of claim 17, wherein the mixture of glucan and gelling agent is cooled to below 40° C.

21. The composition of claim 9, which at 25° C. has a viscosity of at least 1500 cP.

22. The physical support of claim 14, selected from a patch, dressing, plaster, bandage, film or gauze.

23. A gel composition comprising a glucan derived from yeast and a gelling agent, said composition having a melting point (gel to sol) above 37° C., wherein said gelling agent is a cellulose derivative and wherein the gel exists in gel form at 25° C. at pH 4 to 8.

24. The composition of claim 23 wherein the glucan and the gelling agent are present as a hydrogel.

25. The composition of claim 23 wherein the gelling agent is selected from the group consisting of carboxymethyl cellulose, methylcellulose, hydroxypropyl cellulose, hydroxyethyl cellulose, hydroxypropyl methyl cellulose and hydroxypropyl methyl cellulose phthalate.

26. The composition of claim 23, wherein the glucan is derived from *Saccharomyces cerevisiae*.

27. The composition of claim 23 wherein the glucan is a beta glucan comprising a backbone of β-(1,3)-linked glucosyl residues and side chains comprising 2 or more β-(1,3)-linked glucosyl residues, the sidechains being attached to the backbone via a β-(1,6)-linkage.

28. The composition of claim 23 wherein the glucan is essentially free of repetitive β-(1,6)-linked glucosyl residues.

29. The composition of claim 23 which comprises 0.2%-4% glucan and 0.25%-2% gelling agent.

30. The composition of claim 23 which at 25° C. has a viscosity of at least 1000 cP.

31. The composition of claim 23 which comprises about 2% glucan and about 1.5% carboxymethyl cellulose.

32. A method of assisting wound or ulcer healing or treating oral mucositis or cancer in a subject which comprises administering to said subject the composition of claim 23.

33. The method of claim 32 wherein the composition is topically applied to a subject.

34. The method of claim 32 wherein said ulcer is a diabetic ulcer.

35. A physical support having applied thereto or impregnated therein, the composition of claim 23.

36. The physical support of claim 35 selected from the group consisting of a woven, non-woven, knitted, foam or adhesive substrate.

37. A gel composition comprising a glucan derived from yeast and a gelling agent, wherein the gelling agent is a cellulose derivative, wherein the gel exists in gel form at 25° C. at pH 4 to 8, and wherein said gel composition is obtainable by a method which comprises:

a) treating an aqueous solution of glucan molecules derived from yeast, to dissociate the glucan's hydrogen bonds;

b) treating the aqueous solution to reform hydrogen bonds within the glucan;

wherein the gelling agent is added prior to step a) or after step a) but prior to step b).

38. The method of claim 37, wherein step a) comprises heating the aqueous solution of glucan molecules, with or without gelling agent, and step b) comprises cooling the aqueous solution of glucan and gelling agent.

39. The method of claim 38, wherein the aqueous solution, with or without gelling agent, is heated to at least about 100° C.

40. The method of claim 38, wherein the mixture of glucan and gelling agent is rapidly cooled in step b).

41. The method of claim 38, wherein the mixture of glucan and gelling agent is cooled to below 40° C.

42. The composition of claim 30, which at 25° C. has a viscosity of at least 1500 cP.

43. The physical support of claim 35, selected from a patch, dressing, plaster, bandage, film or gauze.

* * * * *